United States Patent
Middleton et al.

(10) Patent No.: US 10,890,579 B2
(45) Date of Patent: Jan. 12, 2021

(54) METHODS AND KITS FOR DETECTING A FUSION MESSENGER RNA TRANSCRIPT OR A POLYPEPTIDE ENCODED BY THE FUSION MESSENGER RNA TRANSCRIPT

(71) Applicant: THE RESEARCH FOUNDATION FOR THE STATE UNIVERSITY OF NEW YORK, Syracuse, NY (US)

(72) Inventors: Frank Middleton, Fayetteville, NY (US); William G. Kerr, Syracuse, NY (US); Sandra Fernandes Denney, Constantia, NY (US)

(73) Assignee: THE RESEARCH FOUNDATION FOR THE STATE UNIVERSITY OF NEW YORK, Syracuse, NY (US)

( * ) Notice: Subject to any disclaimer, the term of this patent is extended or adjusted under 35 U.S.C. 154(b) by 0 days.

(21) Appl. No.: 16/338,843

(22) PCT Filed: Oct. 6, 2017

(86) PCT No.: PCT/US2017/055542
§ 371 (c)(1),
(2) Date: Apr. 2, 2019

(87) PCT Pub. No.: WO2018/067935
PCT Pub. Date: Apr. 12, 2018

(65) Prior Publication Data
US 2020/0041495 A1 Feb. 6, 2020

Related U.S. Application Data

(60) Provisional application No. 62/404,862, filed on Oct. 6, 2016.

(51) Int. Cl.
*C07H 21/04* (2006.01)
*C12Q 1/68* (2018.01)
(Continued)

(52) U.S. Cl.
CPC ....... *G01N 33/5308* (2013.01); *C12Q 1/6883* (2013.01); *C12Q 2600/156* (2013.01); *G01N 2800/065* (2013.01)

(58) Field of Classification Search
None
See application file for complete search history.

(56) References Cited

U.S. PATENT DOCUMENTS

| 2003/0232334 A1 | 12/2003 | Morris et al. |
| 2010/0099083 A1 | 4/2010 | Raelson et al. |
| 2011/0033486 A1 | 2/2011 | Abbas et al. |

OTHER PUBLICATIONS

Klijn et al. (Nature Biotechnology, vol. 33, No. 3, Dec. 8, 2014) (Year: 2014).*

(Continued)

*Primary Examiner* — Jeanine A Goldberg
(74) *Attorney, Agent, or Firm* — Michael Krenicky; Steven A. Wood, Jr.; Garrett Smith

(57) ABSTRACT

The present invention relates to methods and kits for detecting a fusion mRNA transcript or polypeptide encoded by the fusion mRNA transcript. The method includes obtaining a biological sample from a subject and providing one or more reagents capable of binding a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively.

17 Claims, 2 Drawing Sheets
Specification includes a Sequence Listing.

| Sample | Fusion positive | Fusion Negative | Total |
|---|---|---|---|
| SHIP1-Def | 8 | 1 | 89% |
| SHIP1-Suf | 0 | 40 | 0% |
| Controls | 0 | 13 | 0% |

(51) Int. Cl.
   *G01N 33/53*   (2006.01)
   *C12Q 1/6883*   (2018.01)

(56) References Cited

OTHER PUBLICATIONS

Lo et al. (Leukemia Research, vol. 33, pp. 1562-1566, 2009) (Year: 2009).*
Lo et al., "Inactivation of SHIP1 in T-cell Acute Lymphoblastic Leukemia due to Mutation and Extensive Alternative Splicing," Leukemia Research 33:1562-1566 (2009).
McGovern et al., "Genetics of Inflammatory Bowel Diseases," Gastroenterology 149:1163-1176 (2015).
Ngoh et al., "Activity of SHIP, Which Prevents Expression of Interleukin 1b, is Reduced in Patients With Crohn's Disease," Gastroenterology 150:465-476 (2016).
Xavier et al., "Unraveling the Pathogenesis of Inflammatory bowel Disease," Nature 448(7152):427-434 (2007).
PCT International Search Report and Written Opinion for corresponding PCT/US2017/055542, dated Jan. 5, 2018.

* cited by examiner

SEQUENCE LISTING

<160> NUMBER OF SEQ ID NOS: 12

<210> SEQ ID NO 1
<211> LENGTH: 282
<212> TYPE: DNA
<213> ORGANISM: homo sapiens

<400> SEQUENCE: 1
ggcccctccg tgcagtggct ccagcatcac tgaaatcatc aaccccaact acatgggagt      60
ggggcccttt gggccaccaa tgcccctgca cgtgaagcag accttgtccc ctgaccagca     120
gcccacagcc tggagctacg accagccgcc caaggactcc ccgctggggc cctgcagggg     180
agaaagtcct ccgacacctc ccggccagcc gcccatatca cccaagaagt ttttaccctc     240
aacagcaaac cggggtctcc ctcccaggac acaggagtca ag                        282

<210> SEQ ID NO 2
<211> LENGTH: 94
<212> TYPE: DNA
<213> ORGANISM: homo sapiens

<400> SEQUENCE: 2
ataacaaatt gctggaaaag tcagatcttc attcagtgtt ggcccagaaa ctacaggctg      60
aaaagcatga cgtaccaaac aggcacgaga taag                                  94

<210> SEQ ID NO 3
<211> LENGTH: 376
<212> TYPE: DNA

<213> ORGANISM: homo sapiens

<400> SEQUENCE: 3

| | | | | | |
|---|---|---|---|---|---|
| ggcccctccg | tgcagtggct | ccagcatcac | tgaaatcatc | aaccccaact | acatgggagt | 60 |
| ggggcccttt | gggccaccaa | tgccctgca | cgtgaagcag | accttgtccc | ctgaccagca | 120 |
| gcccacagcc | tggagctacg | accagccgcc | caaggactcc | ccgctggggc | cctgcagggg | 180 |
| agaaagtcct | ccgacacctc | ccggccagcc | gcccatatca | cccaagaagt | ttttaccctc | 240 |
| aacagcaaac | cggggtctcc | ctcccaggac | acaggagtca | agataacaaa | ttgctggaaa | 300 |
| agtcagatct | tcattcagtg | ttggcccaga | actacaggc | tgaaaagcat | gacgtaccaa | 360 |
| acaggcacga | gataag | | | | | 376 |

<210> SEQ ID NO 4
<211> LENGTH: 5294
<212> TYPE: DNA
<213> ORGANISM: homo sapiens

<400> SEQUENCE: 4

| | | | | | |
|---|---|---|---|---|---|
| ctagggcatg | gcatcccacg | tgggtgtcag | cacggccgca | gaagaaccac | ttctctggcc | 60 |
| cacccatgcc | tgctaggcca | tgcttcttca | gaagtggcca | caactctcct | gacgtctcca | 120 |
| gagccggtca | ttccacccag | ggggacttca | gctgccactg | acacttcaa | ttgtacgctg | 180 |
| cgaccagttg | ccaggaagga | gagggctggc | aagagagccg | cggcagccgt | ggcagggtgt | 240 |
| aggggacggt | ggacggccag | ggccccccc | tctctctctt | tctctctctc | tctcttgctt | 300 |
| ggtttctgta | atgaggaagt | tctccgcagc | tcagtttcct | ttccctcact | gagcgcctga | 360 |
| aacaggaagt | cagtcagtta | agctggtggc | agcagccgag | gccaccaaga | ggcaacgggc | 420 |
| ggcaggttgc | agtggagggg | cctccgctcc | cctcggtggt | gtgtgggtcc | tggggtgcc | 480 |
| tgccggcccg | gccgaggagg | cccacgccca | ccatggtccc | ctgctggaac | catggcaaca | 540 |
| tcacccgctc | caaggcggag | gagctgcttt | ccaggacagg | caaggacggg | agcttcctcg | 600 |
| tgcgtgccag | cgagtccatc | tcccgggcat | acgcgctctg | cgtgctgtat | cggaattgcg | 660 |
| tttacactta | cagaattctg | cccaatgaag | atgataaatt | cactgttcag | gcatccgaag | 720 |
| gcgtctccat | gaggttcttc | accaagctgg | accagctcat | cgagttttac | aagaaggaaa | 780 |
| acatggggct | ggtgacccat | ctgcaatacc | ctgtgccgct | ggaggaagag | gacacaggcg | 840 |
| acgaccctga | ggaggacaca | gtagaaagtg | tcgtgtctcc | acccgagctg | cccccaagaa | 900 |
| acatcccgct | gactgccagc | tcctgtgagg | ccaaggagg | tccttttttca | aacgagaatc | 960 |
| cccgagcgac | cgagaccagc | cggccgagcc | tctccgagac | attgttccag | cgactgcaaa | 1020 |
| gcatggacac | cagtgggctt | ccagaagagc | atcttaaggc | catccaagat | tatttaagca | 1080 |
| ctcagctcgc | ccaggactct | gaatttgtga | agacagggtc | cagcagtctt | cctcacctga | 1140 |
| agaaactgac | cacactgctc | tgcaaggagc | tctatggaga | agtcatccgg | accctcccat | 1200 |
| ccctggagtc | tctgcagagg | ttatttgacc | agcagctctc | ccgggcctc | cgtccacgtc | 1260 |
| ctcaggttcc | tggtgaggcc | aatcccatca | acatggtgtc | caagctcagc | caactgacaa | 1320 |
| gcctgttgtc | gtccattgaa | gacaaggtca | aggccttgct | gcacgagggt | cctgagtctc | 1380 |
| cgcaccggcc | ctcccttatc | cctccagtca | cctttgaggt | gaaggcagag | tctctgggga | 1440 |
| ttcctcagaa | aatgcagctc | aaagtcgacg | ttgagtctgg | gaaactgatc | attaagaagt | 1500 |
| ccaaggatgg | ttctgaggac | aagttctaca | gccacaagaa | aatcctgcag | ctcattaagt | 1560 |
| cacagaaatt | tctgaataag | ttggtgatct | tggtggaaac | agagaaggag | aagatcctgc | 1620 |

```
ggaaggaata tgttttttgct gactccaaaa agagagaagg cttctgccag ctcctgcagc   1680
agatgaagaa caagcactca gagcagccgg agcccgacat gatcaccatc ttcatcggca   1740
cctggaacat gggtaacgcc ccccctccca agaagatcac gtcctggttt ctctccaagg   1800
ggcagggaaa gacgcgggac gactctgcgg actacatccc ccatgacatt tacgtgatcg   1860
gcacccaaga ggaccccctg agtgagaagg agtggctgga gatcctcaaa cactccctgc   1920
aagaaatcac cagtgtgact tttaaaacag tcgccatcca cacgctctgg aacatccgca   1980
tcgtggtgct ggccaagcct gagcacgaga accggatcag ccacatctgt actgacaacg   2040
tgaagacagg cattgcaaac acactgggga caaggagc cgtgggggtg tcgttcatgt    2100
tcaatggaac ctccttaggg ttcgtcaaca gccacttgac ttcaggaagt gaaaagaaac   2160
tcaggcgaaa ccaaaactat atgaacattc tccggttcct ggccctgggc gacaagaagc   2220
tgagtccctt taacatcact caccgcttca cgcacctctt ctggtttggg gatcttaact   2280
accgtgtgga tctgcctacc tgggaggcag aaaccatcat ccagaaaatc aagcagcagc   2340
agtacgcaga cctcctgtcc cacgaccagc tgctcacaga gaggagggag cagaaggtct   2400
tcctacactt cgaggaggaa gaaatcacgt ttgccccaac ctaccgtttt gagagactga   2460
ctcgggacaa atacgcctac accaagcaga aagcgacagg gatgaagtac aacttgcctt   2520
cctggtgtga ccgagtcctc tggaagtctt atccctggt gcacgtggtg tgtcagtctt    2580
atggcagtac cagcgacatc atgacgagtg accacagccc tgtctttgcc acatttgagg   2640
caggagtcac ttcccagttt gtctccaaga acggtcccgg gactgttgac agccaaggac   2700
agattgagtt tctcaggtgc tatgccacat tgaagaccaa gtcccagacc aaattctacc   2760
tggagttcca ctcgagctgc ttggagagtt ttgtcaagag tcaggaagga gaaaatgaag   2820
aaggaagtga gggggagctg gtggtgaagt ttggtgagac tcttccaaag ctgaagccca   2880
ttatctctga ccctgagtac ctgctagacc agcacatcct catcagcatc aagtcctctg   2940
acagcgacga atcctatggc gagggctgca ttgcccttcg gttagaggcc acagaaacgc   3000
agctgcccat ctacacgcct ctcacccacc atgggagtt gacaggccac ttccaggggg   3060
agatcaagct gcagacctct cagggcaaga cgagggagaa gctctatgac tttgtgaaga   3120
cggagcgtga tgaatccagt gggccaaaga ccctgaagag cctcaccagc cacgacccca   3180
tgaagcagtg ggaagtcact agcagggccc ctccgtgcag tggctccagc atcactgaaa   3240
tcatcaaccc caactacatg ggagtggggc cctttgggcc accaatgccc ctgcacgtga   3300
agcagacctt gtccctgac cagcagccca cagcctggac ctacgaccag ccgcccaagg    3360
actccccgct ggggccctgc aggggagaaa gtcctccgac acctcccggc cagccgccca   3420
tatcacccca gaagttttta ccctcaacag caaaccgggg tctccctccc aggacacagg   3480
agtcaaggcc cagtgacctg gggaagaacg caggggacac gctgcctcag gaggacctgc   3540
cgctgacgaa gcccgagatg tttgagaacc ccctgtatgg gtccctgagt tccttcccta   3600
agcctgctcc caggaaggac caggaatccc ccaaaatgcc gcggaaggaa ccccgccct    3660 gcccggaacc cggcatcttg tcgcccagca tcgtgctcac caaagcccag gaggctgatc   3720
gcggcgaggg gccggcaag caggtgcccg cgccccggct gcgctccttc acgtgctcat    3780
cctctgccga gggcagggcg gccggcgggg acaagagcca agggaagccc aagacccgg    3840 tcagctccca ggccccggtg ccggccaaga ggcccatcaa gccttccaga tcggaaatca   3900
accagcagac cccgcccacc ccgacgccgc ggccgccgct gccagtcaag agcccggcgg   3960
```

-continued

```
tgctgcacct ccagcactcc aagggccgcg actaccgcga caacaccgag ctcccgcatc    4020
acggcaagca ccggccggag gaggggccac cagggcctct aggcaggact gccatgcagt    4080
gaagccctca gtgagctgcc actgagtcgg gagcccagag gaacggcgtg aagccactgg    4140
accctctccc gggacctcct gctggctcct cctgcccagc ttcctatgca aggctttgtg    4200
ttttcaggaa agggcctagc ttctgtgtgg cccacagagt tcactgcctg tgagacttag    4260
caccaagtgc tgaggctgga agaaaaacgc acaccgacg ggcaacaaac agtctgggtc     4320
cccagctcgc tcttggtact tgggacccca gtgcctcgtt gagggcgcca ttctgaagaa    4380
aggaactgca gcgccgattt gagggtggag atatagataa taataatatt aataataata    4440
atggccacat ggatcgaaca ctcatgatgt gccaagtgct gtgctaagtg ctttacgaac    4500
attcgtcata tcaggatgac ctcgagagct gaggctctag ccacctaaaa ccacgtgccc    4560
aaacccacca gtttaaaacg tgtgtgttc ggaggggtga aagcattaag aagcccagtg     4620
ccctcctgga gtgagacaag ggctcggcct taaggagctg aagagtctgg gtagcttgtt    4680
tagggtacaa gaagcctgtt ctgtccagct tcagtgacac aagctgcttt agctaaagtc    4740
ccgcgggttc cggcatggct aggctgagag cagggatcta cctggcttct cagttctttg    4800
gttggaagga gcaggaaatc agctcctatt ctccagtgga gagatctggc ctcagcttgg    4860
gctagagatg ccaaggcctg tgccaggttc cctgtgccct cctcgaggtg ggcagccatc    4920
accagccaca gttaagccaa gccccccaac atgtattcca tcgtgctggt agaagagtct    4980
ttgctgttgc tcccgaaagc cgtgctctcc agcctggctg ccagggaggg tgggcctctt    5040
ggttccaggc tcttgaaata gtgcagcctt ttcttcctat ctctgtggct ttcagctctg    5100
cttccttggt tattaggaga atagatgggt gatgtctttc cttatgttgc ttttttcaaca   5160 tagcagaatt aatgtaggga gctaaatcca gtggtgtgtg tgaatgcaga agggaatgca    5220
ccccacattc ccatgatgga agtctgcgta accaataaat tgtgcctttc tcactcaaaa    5280
aaaaaaaaaa aaaa                                                     5294
```

<210> SEQ ID NO 5
<211> LENGTH: 1189
<212> TYPE: PRT
<213> ORGANISM: homo sapiens

<400> SEQUENCE: 5

```
Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
            20                  25                  30

Ser Glu Ser Ile Ser Arg Ala Tyr Ala Leu Cys Val Leu Tyr Arg Asn
        35                  40                  45

Cys Val Tyr Thr Tyr Arg Ile Leu Pro Asn Glu Asp Asp Lys Phe Thr
    50                  55                  60

Val Gln Ala Ser Glu Gly Val Ser Met Arg Phe Phe Thr Lys Leu Asp
65                  70                  75                  80

Gln Leu Ile Glu Phe Tyr Lys Lys Glu Asn Met Gly Leu Val Thr His
                85                  90                  95

Leu Gln Tyr Pro Val Pro Leu Glu Glu Glu Asp Thr Gly Asp Asp Pro
            100                 105                 110

Glu Glu Asp Thr Val Glu Ser Val Val Ser Pro Pro Glu Leu Pro Pro
        115                 120                 125

Arg Asn Ile Pro Leu Thr Ala Ser Ser Cys Glu Ala Lys Glu Val Pro
```

```
              130                 135                 140
Phe Ser Asn Glu Asn Pro Arg Ala Thr Glu Thr Ser Arg Pro Ser Leu
145                 150                 155                 160

Ser Glu Thr Leu Phe Gln Arg Leu Gln Ser Met Asp Thr Ser Gly Leu
                    165                 170                 175

Pro Glu Glu His Leu Lys Ala Ile Gln Asp Tyr Leu Ser Thr Gln Leu
                180                 185                 190

Ala Gln Asp Ser Glu Phe Val Lys Thr Gly Ser Ser Ser Leu Pro His
            195                 200                 205

Leu Lys Lys Leu Thr Thr Leu Leu Cys Lys Glu Leu Tyr Gly Glu Val
        210                 215                 220

Ile Arg Thr Leu Pro Ser Leu Glu Ser Leu Gln Arg Leu Phe Asp Gln
225                 230                 235                 240

Gln Leu Ser Pro Gly Leu Arg Pro Arg Pro Gln Val Pro Gly Glu Ala
                    245                 250                 255

Asn Pro Ile Asn Met Val Ser Lys Leu Ser Gln Leu Thr Ser Leu Leu
                260                 265                 270

Ser Ser Ile Glu Asp Lys Val Lys Ala Leu Leu His Glu Gly Pro Glu
            275                 280                 285

Ser Pro His Arg Pro Ser Leu Ile Pro Pro Val Thr Phe Glu Val Lys
        290                 295                 300

Ala Glu Ser Leu Gly Ile Pro Gln Lys Met Gln Leu Lys Val Asp Val
305                 310                 315                 320

Glu Ser Gly Lys Leu Ile Ile Lys Lys Ser Lys Asp Gly Ser Glu Asp
                    325                 330                 335

Lys Phe Tyr Ser His Lys Lys Ile Leu Gln Leu Ile Lys Ser Gln Lys
                340                 345                 350

Phe Leu Asn Lys Leu Val Ile Leu Val Glu Thr Glu Lys Glu Lys Ile
            355                 360                 365

Leu Arg Lys Glu Tyr Val Phe Ala Asp Ser Lys Lys Arg Glu Gly Phe
        370                 375                 380

Cys Gln Leu Leu Gln Gln Met Lys Asn Lys His Ser Glu Gln Pro Glu
385                 390                 395                 400

Pro Asp Met Ile Thr Ile Phe Ile Gly Thr Trp Asn Met Gly Asn Ala
                    405                 410                 415

Pro Pro Pro Lys Lys Ile Thr Ser Trp Phe Leu Ser Lys Gly Gln Gly
                420                 425                 430

Lys Thr Arg Asp Asp Ser Ala Asp Tyr Ile Pro His Asp Ile Tyr Val
            435                 440                 445

Ile Gly Thr Gln Glu Asp Pro Leu Ser Glu Lys Glu Trp Leu Glu Ile
        450                 455                 460

Leu Lys His Ser Leu Gln Glu Ile Thr Ser Val Thr Phe Lys Thr Val
465                 470                 475                 480

Ala Ile His Thr Leu Trp Asn Ile Arg Ile Val Val Leu Ala Lys Pro
                    485                 490                 495

Glu His Glu Asn Arg Ile Ser His Ile Cys Thr Asp Asn Val Lys Thr
                500                 505                 510

Gly Ile Ala Asn Thr Leu Gly Asn Lys Gly Ala Val Gly Val Ser Phe
            515                 520                 525

Met Phe Asn Gly Thr Ser Leu Gly Phe Val Asn Ser His Leu Thr Ser
        530                 535                 540

Gly Ser Glu Lys Lys Leu Arg Arg Asn Gln Asn Tyr Met Asn Ile Leu
545                 550                 555                 560
```

-continued

```
Arg Phe Leu Ala Leu Gly Asp Lys Lys Leu Ser Pro Phe Asn Ile Thr
                565                 570                 575

His Arg Phe Thr His Leu Phe Trp Phe Gly Asp Leu Asn Tyr Arg Val
            580                 585                 590

Asp Leu Pro Thr Trp Glu Ala Glu Thr Ile Ile Gln Lys Ile Lys Gln
        595                 600                 605

Gln Gln Tyr Ala Asp Leu Leu Ser His Asp Gln Leu Leu Thr Glu Arg
    610                 615                 620

Arg Glu Gln Lys Val Phe Leu His Phe Glu Glu Glu Ile Thr Phe
625                 630                 635                 640

Ala Pro Thr Tyr Arg Phe Glu Arg Leu Thr Arg Asp Lys Tyr Ala Tyr
                645                 650                 655

Thr Lys Gln Lys Ala Thr Gly Met Lys Tyr Asn Leu Pro Ser Trp Cys
            660                 665                 670

Asp Arg Val Leu Trp Lys Ser Tyr Pro Leu Val His Val Val Cys Gln
        675                 680                 685

Ser Tyr Gly Ser Thr Ser Asp Ile Met Thr Ser Asp His Ser Pro Val
    690                 695                 700

Phe Ala Thr Phe Glu Ala Gly Val Thr Ser Gln Phe Val Ser Lys Asn
705                 710                 715                 720

Gly Pro Gly Thr Val Asp Ser Gln Gln Ile Glu Phe Leu Arg Cys
                725                 730                 735

Tyr Ala Thr Leu Lys Thr Lys Ser Gln Thr Lys Phe Tyr Leu Glu Phe
            740                 745                 750

His Ser Ser Cys Leu Glu Ser Phe Val Lys Ser Gln Glu Gly Glu Asn
        755                 760                 765

Glu Glu Gly Ser Glu Gly Glu Leu Val Val Lys Phe Gly Glu Thr Leu
    770                 775                 780

Pro Lys Leu Lys Pro Ile Ile Ser Asp Pro Glu Tyr Leu Leu Asp Gln
785                 790                 795                 800

His Ile Leu Ile Ser Ile Lys Ser Ser Asp Ser Asp Glu Ser Tyr Gly
                805                 810                 815

Glu Gly Cys Ile Ala Leu Arg Leu Glu Ala Thr Glu Thr Gln Leu Pro
            820                 825                 830

Ile Tyr Thr Pro Leu Thr His His Gly Glu Leu Thr Gly His Phe Gln
        835                 840                 845

Gly Glu Ile Lys Leu Gln Thr Ser Gln Gly Lys Thr Arg Glu Lys Leu
    850                 855                 860

Tyr Asp Phe Val Lys Thr Glu Arg Asp Glu Ser Ser Gly Pro Lys Thr
865                 870                 875                 880

Leu Lys Ser Leu Thr Ser His Asp Pro Met Lys Gln Trp Glu Val Thr
                885                 890                 895

Ser Arg Ala Pro Pro Cys Ser Gly Ser Ser Ile Thr Glu Ile Ile Asn
            900                 905                 910

Pro Asn Tyr Met Gly Val Gly Pro Phe Gly Pro Pro Met Pro Leu His
        915                 920                 925

Val Lys Gln Thr Leu Ser Pro Asp Gln Pro Thr Ala Trp Ser Tyr
    930                 935                 940

Asp Gln Pro Pro Lys Asp Ser Pro Leu Gly Pro Cys Arg Gly Glu Ser
945                 950                 955                 960

Pro Pro Thr Pro Pro Gly Gln Pro Pro Ile Ser Pro Lys Lys Phe Leu
                965                 970                 975
```

```
Pro Ser Thr Ala Asn Arg Gly Leu Pro Pro Arg Thr Gln Glu Ser Arg
            980                 985                 990

Pro Ser Asp Leu Gly Lys Asn Ala  Gly Asp Thr Leu Pro  Gln Glu Asp
        995                 1000                 1005

Leu Pro Leu Thr Lys Pro Glu  Met Phe Glu Asn Pro  Leu Tyr Gly
        1010                1015                1020

Ser Leu Ser Ser Phe Pro Lys  Pro Ala Pro Arg Lys  Asp Gln Glu
        1025                1030                1035

Ser Pro Lys Met Pro Arg Lys  Glu Pro Pro Cys  Pro Glu Pro
        1040                1045            1050

Gly Ile Leu Ser Pro Ser Ile  Val Leu Thr Lys Ala  Gln Glu Ala
        1055                1060                1065

Asp Arg Gly Glu Gly Pro Gly  Lys Gln Val Pro Ala  Pro Arg Leu
        1070                1075                1080

Arg Ser Phe Thr Cys Ser Ser  Ser Ala Glu Gly Arg  Ala Ala Gly
        1085                1090                1095

Gly Asp Lys Ser Gln Gly Lys  Pro Lys Thr Pro Val  Ser Ser Gln
        1100                1105                1110

Ala Pro Val Pro Ala Lys Arg  Pro Ile Lys Pro Ser  Arg Ser Glu
        1115                1120                1125

Ile Asn Gln Gln Thr Pro Pro  Thr Pro Thr Pro Arg  Pro Pro Leu
        1130                1135                1140

Pro Val Lys Ser Pro Ala Val  Leu His Leu Gln His  Ser Lys Gly
        1145                1150                1155

Arg Asp Tyr Arg Asp Asn Thr  Glu Leu Pro His His  Gly Lys His
        1160                1165                1170

Arg Pro Glu Glu Gly Pro Pro  Gly Pro Leu Gly Arg  Thr Ala Met
        1175                1180                1185

Gln
```

<210> SEQ ID NO 6
<211> LENGTH: 3407
<212> TYPE: DNA
<213> ORGANISM: homo sapiens

<400> SEQUENCE: 6

```
actagcgagc gccctgcgta ggcaccggct cctgagcccg tgcttcgggt gaggggcgg      60
gtcttccggc cctctcgaaa atcatttccg gcatgagccg gaagaccgtc ccggatggcc    120
tcggggactg ccagtgtgtg gaggtgagct ccgggattgc cggcattccc gcttctgctg    180
gttgcttcat gctgcaggct gcggccgtca gccctcgctc gcattggtgg cgctgaggtg    240
ccggggcagc aagtgacatg tcgtcgggcc tccgcgccgc tgacttcccc cgctggaagc    300
gccacatctc ggagcaactg aggcgccggg accggctgca gagacaggcg ttcgaggaga    360
tcatcctgca gtataacaaa ttgctggaaa agtcagatct tcattcagtg ttggcccaga    420
aactacaggc tgaaaagcat gacgtaccaa acaggcacga gataagtccc ggacatgatg    480
gcacatggaa tgacaatcag ctacaagaaa tggcccaact gaggattaag caccaagagg    540
aactgactga attacacaag aaacgtgggg agctcaactg gtgattgacc tgaataacca    600
aatgcagcgg aaggacaggg agatgcagat gaatgaagca aaaattgcag aatgtttgca    660
gactatctct gacctggaga cggagtgcct agacctgcgc actaagcttt gtgaccttga    720
aagagccaac cagaccctga aggatgaata tgatgccctg cagatcactt ttactgcctt    780
ggagggaaaa ctgaggaaaa ctacggaaga gaaccaggag ctggtcacca gatggatggc    840
```

```
tgagaaagcc caggaagcca atcggcttaa tgcagagaat gaaaaagact ccaggaggcg    900
gcaagcccgg ctgcagaaag agcttgcaga agcagcaaag gaacctctac cagtcgaaca    960
ggatgatgac attgaggtca ttgtggatga aacttctgat cacacagaag agacctctcc   1020
tgtgcgagcc atcagcagag cagccactaa gcgactctcg cagcctgctg gaggccttct   1080
ggattctatc actaatatct ttgggagacg ctctgtctct tccttcccag tcccccagga   1140
caatgtggat actcatcctg gttctggtaa agaagtgagg gtaccagcta ctgccttgtg   1200
tgtcttcgat gcacatgatg gggaagtcaa cgctgtgcag ttcagtccag gttcccggtt   1260
actggccact ggaggcatgg accgcagggt taagctttgg gaagtatttg agaaaaatg    1320
tgagttcaag ggttccctat ctggcagtaa tgcaggaatt acaagcattg aatttgatag   1380
tgctggatct tacctcttag cagcttcaaa tgattttgca agccgaatct ggactgtgga   1440
tgattatcga ttacggcaca cactcacggg acacagtggg aaagtgctgt ctgctaagtt   1500
cctgctggac aatgcgcgga ttgtctcagg aagtcacgac cggactctca aactctggga   1560
tctacgcagc aaagtctgca taaagacagt gtttgcagga tccagttgca atgatattgt   1620
ctgcacagag caatgtgtaa tgagtggaca ttttgacaag aaaattcgtt tctgggacat   1680
tcgatcagag agcatagttc gagagatgga gctgttggga aagattactg ccctggactt   1740
aaacccagaa aggactgagc tcctgagctg ctcccgtgat gacttgctaa agttattga    1800
tctccgaaca aatgctatca agcagacatt cagtgcacct gggttcaagt gcggctctga   1860
ctggaccaga gttgtcttca gccctgatgg cagttacgtg gcggcaggct ctgctgaggg   1920
ctctctgtat atctggagtg tgctcacagg gaaagtggaa aaggttcttt caaagcagca   1980
cagctcatcc atcaatgcgg tggcgtggtc gccctctggc tcgcacgttg tcagtgtgga   2040
caaaggatgc aaagctgtgc tgtgggcaca gtactgacgg ggctctcagg gctgggagga   2100
ccccagtgcc ctcctcagaa gaagcacatg ggctcctgca gccctgtcct ggcaggtgat   2160
gtgctgggta tagcatggac ctcccagaga agctcaagct atgtggcact gtagctttgc   2220
cgtgaatggg atttctgaag atttgactga ggtctctctt ggcctggaag aataacactg   2280
aaaaaacctg acgctgcggt cacttagcag aggctcaggt tcttgccttg ggaaacacta   2340
ctagctctga ccttccatac ctcacttggg ggagcacagg gccccgctgg gcctcctcac   2400
caacggcagt gccaaaatca gcccccacat caaggtggtg ttctctgtgc tttctctcgt   2460
ccttccaaag tcggttctgg cctaacgcat gtcccaacac cttgggttca tttgcccggt   2520
gaactcactt taagcattgg attaacgaaa actcccgaac tacagacccc tccctggtgg   2580
gttgcatgaa tgtgtctcat tactgctgaa atgtcctcac atctctttca ctgttcttca   2640
gagctttctg gctctctttc ccccacaaaa ttcgacatat ttaaaaatct ccgtgtggct   2700
ttaaaaaatg gttttttgtt tttttgtttt tttgaggtgg gagaggatgt gtgaaaatct   2760
tttccaggga aatgggttcg ctgcagaggt aaggatgtgt tcctgtatcg atctgcagac   2820
acccagaagg tgggtgcaca ctgcatgctt ggggtgcca agggattcga acctccaac    2880
atacttgtct gaaggtggtg attctggcca tggcccctct gccaagcctg tgtgcgatgc   2940
ccttggtgct ttagtgcaag aagcctaggc tcagaagcac agcagcgcca tctttccgtt   3000
tcaggggttg tgatgaaggc caaggaaaaa catttatctt tactatttta cctacgtata   3060
aagtttagt tcattgggtg tgcgaaacac ccttttttatc acttttaaat ttgcacttta   3120
tttttttct tccatgcttg ttctctggac atttgggat gtgagtgtta gagctggtga    3180
```

-continued

```
gagaggagtc aggtggcctt cccaccgatg gtcctggcct ccacctgccc tctcttccct    3240
gcctgatcac cgctttccaa tttgcccttc agagaactta agtcaaggag agttgaaatt    3300
cacaggccag ggcacatctt ttatttattt cattatgttg gccaacagaa cttgattgta    3360
aataataata aagaaatctg ttatatactt ttcaaactcc aaaaaaa                  3407
```

<210> SEQ ID NO 7
<211> LENGTH: 491
<212> TYPE: PRT
<213> ORGANISM: homo sapiens

<400> SEQUENCE: 7

```
Met Gln Arg Lys Asp Arg Glu Met Gln Met Asn Glu Ala Lys Ile Ala
1               5                   10                  15

Glu Cys Leu Gln Thr Ile Ser Asp Leu Glu Thr Glu Cys Leu Asp Leu
            20                  25                  30

Arg Thr Lys Leu Cys Asp Leu Glu Arg Ala Asn Gln Thr Leu Lys Asp
        35                  40                  45

Glu Tyr Asp Ala Leu Gln Ile Thr Phe Thr Ala Leu Glu Gly Lys Leu
    50                  55                  60

Arg Lys Thr Thr Glu Glu Asn Gln Glu Leu Val Thr Arg Trp Met Ala
65                  70                  75                  80

Glu Lys Ala Gln Glu Ala Asn Arg Leu Asn Ala Glu Asn Glu Lys Asp
                85                  90                  95

Ser Arg Arg Arg Gln Ala Arg Leu Gln Lys Glu Leu Ala Glu Ala Ala
            100                 105                 110

Lys Glu Pro Leu Pro Val Glu Gln Asp Asp Ile Glu Val Ile Val
        115                 120                 125

Asp Glu Thr Ser Asp His Thr Glu Glu Thr Ser Pro Val Arg Ala Ile
    130                 135                 140

Ser Arg Ala Ala Thr Lys Arg Leu Ser Gln Pro Ala Gly Gly Leu Leu
145                 150                 155                 160

Asp Ser Ile Thr Asn Ile Phe Gly Arg Arg Ser Val Ser Ser Phe Pro
                165                 170                 175

Val Pro Gln Asp Asn Val Asp Thr His Pro Gly Ser Gly Lys Glu Val
            180                 185                 190

Arg Val Pro Ala Thr Ala Leu Cys Val Phe Asp Ala His Asp Gly Glu
        195                 200                 205

Val Asn Ala Val Gln Phe Ser Pro Gly Ser Arg Leu Leu Ala Thr Gly
    210                 215                 220

Gly Met Asp Arg Arg Val Lys Leu Trp Glu Val Phe Gly Glu Lys Cys
225                 230                 235                 240

Glu Phe Lys Gly Ser Leu Ser Gly Ser Asn Ala Gly Ile Thr Ser Ile
                245                 250                 255

Glu Phe Asp Ser Ala Gly Ser Tyr Leu Leu Ala Ala Ser Asn Asp Phe
            260                 265                 270

Ala Ser Arg Ile Trp Thr Val Asp Asp Tyr Arg Leu Arg His Thr Leu
        275                 280                 285

Thr Gly His Ser Gly Lys Val Leu Ser Ala Lys Phe Leu Leu Asp Asn
    290                 295                 300

Ala Arg Ile Val Ser Gly Ser His Asp Arg Thr Leu Lys Leu Trp Asp
305                 310                 315                 320

Leu Arg Ser Lys Val Cys Ile Lys Thr Val Phe Ala Gly Ser Ser Cys
                325                 330                 335
```

Asn Asp Ile Val Cys Thr Glu Gln Cys Val Met Ser Gly His Phe Asp
            340                 345                 350

Lys Lys Ile Arg Phe Trp Asp Ile Arg Ser Glu Ser Ile Val Arg Glu
        355                 360                 365

Met Glu Leu Leu Gly Lys Ile Thr Ala Leu Asp Leu Asn Pro Glu Arg
    370                 375                 380

Thr Glu Leu Leu Ser Cys Ser Arg Asp Asp Leu Leu Lys Val Ile Asp
385                 390                 395                 400

Leu Arg Thr Asn Ala Ile Lys Gln Thr Phe Ser Ala Pro Gly Phe Lys
                405                 410                 415

Cys Gly Ser Asp Trp Thr Arg Val Val Phe Ser Pro Asp Gly Ser Tyr
            420                 425                 430

Val Ala Ala Gly Ser Ala Glu Gly Ser Leu Tyr Ile Trp Ser Val Leu
        435                 440                 445

Thr Gly Lys Val Glu Lys Val Leu Ser Lys Gln His Ser Ser Ser Ile
    450                 455                 460

Asn Ala Val Ala Trp Ser Pro Ser Gly Ser His Val Val Ser Val Asp
465                 470                 475                 480

Lys Gly Cys Lys Ala Val Leu Trp Ala Gln Tyr
                485                 490

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
cccatatcac ccaagaagtt                                               20

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
aaatacctta tctcgtgcct g                                             21

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
taccctcaac agcaaacc                                                 18

<210> SEQ ID NO 11
<211> LENGTH: 17
<212> TYPE: DNA
<213> ORGANISM: Artificial
<220> FEATURE:
<223> OTHER INFORMATION: Primer

<400> SEQUENCE: 11
gggccaacac tgaatga                                                  17

```
<210> SEQ ID NO 12
<211> LENGTH: 26
<212> TYPE: DNA
<213> ORGANISM: Artificial
<220> FEATURE:
<223> OTHER INFORMATION: Probe for HEX label

<400> SEQUENCE: 12
cctcccagga cacaggagtc aagata                                          26
```

US 10,890,579 B2

METHODS AND KITS FOR DETECTING A FUSION MESSENGER RNA TRANSCRIPT OR A POLYPEPTIDE ENCODED BY THE FUSION MESSENGER RNA TRANSCRIPT

This application claims the priority benefit of U.S. Provisional Patent Application Ser. No. 62/404,862, filed Oct. 6, 2016, which is hereby incorporated by reference in its entirety.

This invention was made with government support under grant numbers HL107127 and HL072523 awarded by the National Institutes of Health. The government has certain rights in this invention.

FIELD OF THE INVENTION

The present invention relates to methods and kits for detecting a fusion messenger RNA transcript or a polypeptide encoded by the fusion messenger RNA transcript.

BACKGROUND OF THE INVENTION

Inflammatory bowel disease (IBD) refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia, e.g. iron deficiency anemia and anemia of chronic disease or of chronic inflammation. The etiology or etiologies of IBD are, unfortunately, unclear.

Ulcerative colitis refers to a chronic, non-specific, inflammatory, and ulcerative disease having manifestations primarily in the colonic mucosa. It is frequently characterized by bloody diarrhea, abdominal cramps, blood and mucus in the stools, malaise, fever, anemia, anorexia, weight loss, leukocytosis, hypoalbuminemia, and an elevated erythrocyte sedimentation rate (ESR). Complications can include hemorrhage, toxic colitis, toxic megacolon, occasional rectovaginal fistulas, and an increased risk for the development of colon cancer.

Ulcerative colitis is also associated with complications distant from the colon, such as arthritis, ankylosing spondylitis, sacroileitis, posterior uveitis, erythema nodosum, pyoderma gangrenosum, and episcleritis. Treatment varies considerably with the severity and duration of the disease. For instance, fluid therapy to prevent dehydration and electrolyte imbalance is frequently indicated in a severe attack. Additionally, special dietary measures are sometimes useful. Medications include various corticosteroids, sulphasalazine and some of its derivatives, and possibly immunosuppressive drugs.

Crohn's Disease shares many features in common with ulcerative colitis. Crohn's Disease is distinguishable in that lesions tend to be sharply demarcated from adjacent normal bowel, in contrast to the lesions of ulcerative colitis which are fairly diffuse. Additionally, Crohn's Disease predominately afflicts the ileum (ileitis) and the ileum and colon (ileocolitis). In some cases, the colon alone is diseased (granulomatous colitis) and sometimes the entire small bowel is involved (jejunoileitis). In rare cases, the stomach, duodenum, or esophagus are involved. Lesions include a sarcoid-type epithelioid granuloma in roughly half of the clinical cases. Lesions of Crohn's Disease can be transmural including deep ulceration, edema, and fibrosis, which can lead to obstruction and fistula formation as well as abscess formation. This contrasts with ulcerative colitis which usually yields much shallower lesions, although occasionally the complications of fibrosis, obstruction, fistula formation, and abscesses are seen in ulcerative colitis as well.

Treatment is similar for both diseases and includes steroids, sulphasalazine and its derivatives, and immunosuppressive drugs such as cyclosporin A, mercaptopurine and azathioprine.

The severe complications of IBD can be seriously debilitating, and eventually may lead to death. Thus, a need exists for effective diagnosis and management of treatment.

The present invention is directed to overcoming these and other deficiencies in the art.

SUMMARY OF THE INVENTION

A first aspect of the present invention relates to a method of detecting a fusion mRNA transcript or polypeptide encoded by the fusion mRNA transcript. The method includes obtaining a biological sample from a subject and providing one or more reagents capable of binding a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively. The biological sample is contacted with the reagents under conditions effective to permit binding to the fusion mRNA transcript or polypeptide encoded by the fusion mRNA transcript, if present, in the biological sample. The fusion mRNA transcript or polypeptide encoded by the fusion mRNA transcript in the sample is then detected.

The method of detecting a fusion mRNA transcript or polypeptide encoded by the fusion mRNA transcript, in accordance with the first aspect of the present invention, can be used in diagnosing the subject with IBD (e.g., Crohn's Disease or Ulcerative Colitis) if a fusion mRNA transcript or polypeptide is detected.

Following detection of a fusion mRNA transcript or polypeptide encoded by the fusion mRNA transcript, in accordance with the first aspect of the present invention, the subject with IBD (e.g., Crohn's Disease or Ulcerative Coliti) can be treated for such diseases.

A second aspect of the present invention relates to a kit suitable for diagnosing IBD. The kit includes one or more reagents suitable for detecting a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively.

The method of detecting a fusion mRNA transcript, in accordance with the first aspect of the present invention, can be used to identify subjects having a risk of Crohn's disease and to identify, among subjects diagnosed with Crohn's disease, those who have a higher probability of requiring one or more surgical resections or having an IBD related neoplasia in the future.

BRIEF DESCRIPTION OF THE DRAWINGS

FIG. 1A shows RT-PCR analysis of total RNA using primers specifically targeting the fusion transcript. The primers were used to screen a subset of the IBD cohort, and RNA-Seq analysis revealed the presence of a fusion transcript between SHIP1 and downstream ATG16L1 in several but not all SHIP1-deficient subjects (8 out of 9). FIG. 1B shows the fusion transcript was not observed in 53 of the SHIP1-sufficient and healthy control subjects, while it was observed in 89% of SHIP1-deficient samples (8 of 9). This represents a highly-significant association to the SHIP1-deficient phenotype with an Odds Ratio (OR) of 153.0 (95% CI: 5.562 to 4209, p<0.0001) compared to the 13 controls, and an OR of 606.3 (95% CI: 22.76-16150, p<0.0001) compared to all available SHIP1-sufficient IBD and control subjects (n=53). FIG. 1C shows the junction of exon 25 of SHIP1 mRNA to exon 2 of ATG16L1 as confirmed by sequencing of the fusion RT-PCR product.

FIGS. 2E-2F show the frequency of live and CD3$^+$ T cells (FIG. 2E) and CD4$^+$ T cells (FIG. 2F) in WBC of CD4CreSHIP$^{flox/flox}$ and SHIP$^{flox/flox}$ control mice (One-tailed t-test *p<0.001, n=12/group).

DETAILED DESCRIPTION OF THE INVENTION

Figures 1A, 1B, 1C:
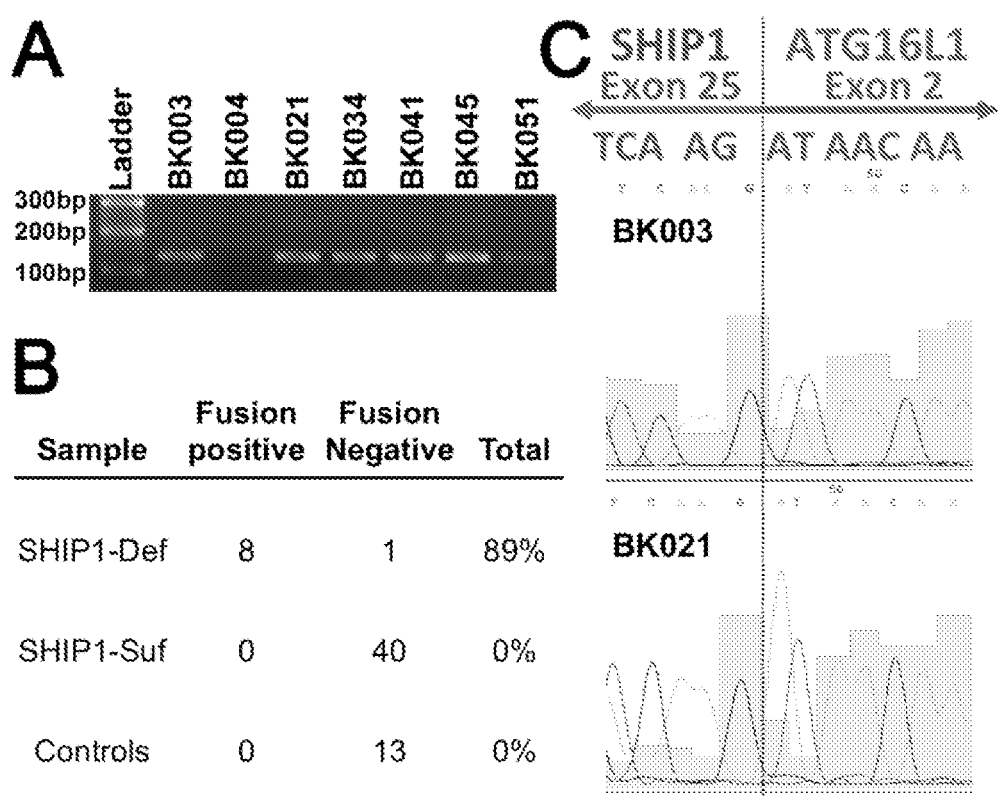
FIGS. 1A-1C demonstrate RNA-Seq analysis uncovered a novel fusion mRNA transcript that links SHIP1 exon 25 to ATG16L1 exon 2 in SHIP1-deficient subjects.

The present application discloses methods for detecting the presence of a INPP5D-ATG16L1 fusion mRNA (messenger RNA), or truncated protein translated therefrom, whose presence is diagnostic of both inflammatory bowel disease (IBD) and its severity, such as the likelihood that a subject suffering from IBD (or one of its more severe variations, such as Crohn's Disease (CD) or ulcerative colitis (UC)) will require aggressive treatment such as surgical resection. The INPP5D-ATG16L1 fusion mRNA comprises a region where the 3' end of the mRNA transcript of exon 25 of INPP5D is fused (connected directly or indirectly) to the 5' end of the mRNA transcript of exon 2 of ATG16L1, creating a unique stretch of mRNA that can be detected using a number of known methods. The truncated INPP5D-ATG16L1 fusion protein comprises INPP5D protein truncated at 991 amino acids with an apparent molecular weight of 112 kDa. The truncated protein may contain a portion of ATG16L1 protein, starting with the portion expressed by exon 2.

The present invention relates to detecting the presence of an INPP5D-ATG16L1 fusion mRNA that is diagnostic of IBD and related conditions in IBD patients and may identify those with impending severe disease that will ultimately require surgical resections. The INPP5D-ATG16L1 fusion mRNA comprises a region where the 3' end of the mRNA transcript of exon 25 of INPP5D is fused (connected directly) to the 5' end of the mRNA transcript of exon2 of ATG16L1, creating a unique stretch of mRNA that can be detected using a number of known methods. INPP5D-ATG16L1 fusion mRNA may comprise all or portions of the WT INPP5D mRNA up to the mRNA transcribed by exons 1-24 of WT INPP5D and all or portions of the WT ATG16L1 mRNA up to the mRNA transcribed by exons 2-18.

Thus, a first aspect of the present invention relates to a method of detecting a fusion mRNA transcript or polypeptide encoded by the fusion mRNA transcript. The method includes obtaining a biological sample from a subject and providing one or more reagents capable of binding a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively. The biological sample is contacted with the reagents under conditions effective to permit binding to the fusion mRNA transcript or polypeptide encoded by the fusion mRNA transcript, if present, in the biological sample. The fusion mRNA transcript or polypeptide encoded by the fusion mRNA transcript in the sample is then detected.

As used herein, the term "INPP5D-ATG16L" or "INPP5D-ATG16L1 fusion" refers to a chimeric messenger RNA, a truncated protein or a chimeric protein resulting from the fusion of at least a portion of INPP5D transcript ending with exon 25 to at least a portion of a second transcript starting with exon 2.

By the terms "INPP5D-ATG16L1 fusion protein" or "INPP5D-ATG16L1 fusion polypeptide" and "truncated SHIP1" and "truncated INPP5D" is meant a translation product of a INPP5D-ATG16L1 fusion mRNA such as INPP5D protein truncated at 991 amino acids with an apparent molecular weight of 112 kDa, or a protein that shares at least 65% (but preferably 75, 80, 85, 90, 95, 96, 97, 98, or 99%) amino acid sequence identity with the foregoing and incorporates a portion of the N-terminus of the ATG16L1 protein.

"Exon 2" refers to the nucleotides that are transcribed from exon 2 of ATG16L1, and to amino acids that are translated from the exon 2 portion of chimeric INPP5D-ATG16L1 fusion mRNA. "Exon 25" refers to the nucleotides that are transcribed from exon 25 of INPP5D, and to amino acids that are translated from the exon 25 portion of chimeric INPP5D-ATG16L1 fusion mRNA. Due to a transposition in translation, the amino acids translated from the exon 25 and exon 2 portions of the INPP5D-ATG16L1 fusion mRNA may differ from the amino acids translated from WT INPP5D and ATG16L1, resulting in the truncated INPP5D protein described above.

Exon 25 (5'-3') of INPP5D has the nucleotide sequence of SEQ ID NO: 1 below.

SEQ ID NO: 1
GGCCCCTCCGTGCAGTGGCTCCAGCATCACTGAAATCATCAACCCCAACT

ACATGGGAGTGGGGCCCTTTGGGCCACCAATGCCCCTGCACGTGAAGCAG

ACCTTGTCCCCTGACCAGCAGCCCACAGCCTGGAGCTACGACCAGCCGCC

CAAGGACTCCCCGCTGGGGCCCTGCAGGGGAGAAAGTCCTCCGACACCTC

CCGGCCAGCCGCCCATATCACCCAAGAAGTTTTTACCCTCAACAGCAAAC

CGGGGTCTCCCTCCCAGGACACAGGAGTCAAG

Exon 2 (5'-3') of ATG16L1 has the nucleotide sequence of SEQ ID NO: 2 below.

SEQ ID NO: 2
ATAACAAATTGCTGGAAAAGTCAGATCTTCATTCAGTGTTGGCCCAGAAA

CTACAGGCTGAAAAGCATGACGTACCAAACAGGCACGAGATAAG

The fusion point or location of the INPP5D-ATG16L1 fusion mRNA is indicated in SEQ ID NO: 3 by the change in font from regular capital letters to bold, italicized capital letters and emphasized by the underlining. It is between the nucleotides transcribed from INPP5D's exon 25 and the nucleotides transcribed from ATG16L1's exon 2. Although both exons may have variants which have somewhat different sequences than those in SEQ ID NO: 3 (which contains the sequences SEQ ID NO: 1 and SEQ ID NO: 2), in SEQ ID NO: 3, the fusion point is between the 10 nucleotide stretch AGGAGTCAAG, which are the final 10 nucleotides transcribed from INPP5D's exon 25, and ATAACAAATT, which are the final 10 nucleotides transcribed from ATG16L1's exon 2. INPP5D-ATG16L1 fusion mRNA will always contain nucleotides transcribed from both INPP5D and from ATG16L1.

SEQ ID NO: 3
GGCCCCTCCGTGCAGTGGCTCCAGCATCACTGAAATCATCAACCCCAACT

ACATGGGAGTGGGGCCCTTTGGGCCACCAATGCCCCTGCACGTGAAGCAG

ACCTTGTCCCCTGACCAGCAGCCCACAGCCTGGAGCTACGACCAGCCGCC

CAAGGACTCCCCGCTGGGGCCCTGCAGGGGAGAAAGTCCTCCGACACCTC

CCGGCCAGCCGCCCATATCACCCAAGAAGTTTTTACCCTCAACAGCAAAC

CGGGGTCTCCCTCCCAGGACACAGGAGTCAAG

*<u>ATAACAAATTGCTGGAAAAGTCAGATCTTCATTCAGTG</u>*

*<u>TTGGCCCAGAAACTACAGGCTGAAAAGCATG</u>*

*<u>ACGTACCAAACAGGCACGAGATAAG</u>*

The complete nucleic acid sequence of INNP5D is shown as SEQ ID NO: 4 below.

```
CTAGGGCATG GCATCCCACG TGGGTGTCAG CACGGCCGCA

GAAGAACCAC TTCTCTGCC CACCCATGCC TGCTAGGCCA

TGCTTCTTCA GAAGTGGCCA CAACTCTCCT GACGTCTCCA

GAGCCGGTCA TTCCACCCAG GGGGACTTCA GCTGCCACTG

GACACTTCAA TTGTACGCTG CGACCAGTTG CCAGGAAGGA

GAGGGCTGGC AAGAGAGCCG CGGCAGCCGT GGCAGGGTGT

AGGGGACGGT GGACGGCCAG GGCCCCCCCC TCTCTCTCTT

TCTCTCTCTC TCTCTTGCTT GGTTTCTGTA ATGAGGAAGT

TCTCCGCAGC TCAGTTTCCT TTCCCTCACT GAGCGCCTGA

AACAGGAAGT CAGTCAGTTA AGCTGGTGGC AGCAGCCGAG

GCCACCAAGA GGCAACGGGC GGCAGGTTGC AGTGGAGGGG

CCTCCGCTCC CCTCGGTGGT GTGTGGGTCC TGGGGGTGCC

TGCCGGCCCG GCCGAGGAGG CCCACGCCCA CCATGGTCCC
```

-continued
```
CTGCTGGAAC CATGGCAACA TCACCCGCTC CAAGGCGGAG

GAGCTGCTTT CCAGGACAGG CAAGGACGGG AGCTTCCTCG

TGCGTGCCAG CGAGTCCATC TCCCGGGCAT ACGCGCTCTG

CGTGCTGTAT CGGAATTGCG TTTACACTTA CAGAATTCTG

CCCAATGAAG ATGATAAATT CACTGTTCAG GCATCCGAAG

GCGTCTCCAT GAGGTTCTTC ACCAAGCTGG ACCAGCTCAT

CGAGTTTTAC AAGAAGGAAA ACATGGGGCT GGTGACCCAT

CTGCAATACC CTGTGCCGCT GGAGGAAGAG GACACAGGCG

ACGACCCTGA GGAGGACACA GTAGAAAGTG TCGTGTCTCC

ACCCGAGCTG CCCCCAAGAA ACATCCCGCT GACTGCCAGC

TCCTGTGAGG CCAAGGAGGT TCCTTTTTCA AACGAGAATC

CCCGAGCGAC CGAGACCAGC CGGCCGAGCC TCTCCGAGAC

ATTGTTCCAG CGACTGCAAA GCATGGACAC CAGTGGGCTT

CCAGAAGAGC ATCTTAAGGC CATCCAAGAT TATTTAAGCA

CTCAGCTCGC CCAGGACTCT GAATTTGTGA AGACAGGGTC

CAGCAGTCTT CCTCACCTGA AGAAACTGAC CACACTGCTC

TGCAAGGAGC TCTATGGAGA AGTCATCCGG ACCCTCCCAT

CCCTGGAGTC TCTGCAGAGG TTATTTGACC AGCAGCTCTC

CCCCGGGCCTC CGTCCACGTC CTCAGGTTCC TGGTGAGGCC

AATCCCATCA ACATGGTGTC CAAGCTCAGC CAACTGACAA

GCCTGTTGTC GTCCATTGAA GACAAGGTCA AGGCCTTGCT

GCACGAGGGT CCTGAGTCTC CGCACCGGCC CTCCCTTATC

CCTCCAGTCA CCTTTGAGGT GAAGGCAGAG TCTCTGGGGA

TTCCTCAGAA AATGCAGCTC AAAGTCGACG TTGAGTCTGG

GAAACTGATC ATTAAGAAGT CCAAGGATGG TTCTGAGGAC

AAGTTCTACA GCCACAAGAA AATCCTGCAG CTCATTAAGT

CACAGAAATT TCTGAATAAG TTGGTGATCT TGGTGGAAAC

AGAGAAGGAG AAGATCCTGC GGAAGGAATA TGTTTTTGCT

GACTCCAAAA AGAGAGAAGG CTTTCTGCCAG CTCCTGCAGC

AGATGAAGAA CAAGCACTCA GAGCAGCCGG AGCCCGACAT

GATCACCATC TTCATCGGCA CCTGGAACAT GGGTAACGCC

CCCCCTCCCA AGAAGATCAC GTCCTGGTTT CTCTCCAAGG

GGCAGGGAAA GACGCGGGAC GACTCTGCGG ACTACATCCC

CCATGACATT TACGTGATCG GCACCCAAGA GGACCCCCTG

AGTGAGAAGG AGTGGCTGGA GATCCTCAAA CACTCCCTGC

AAGAAATCAC CAGTGTGACT TTTAAAACAG TCGCCATCCA

CACGCTCTGG AACATCCGCA TCGTGGTGCT GGCCAAGCCT

GAGCACGAGA ACCGGATCAG CCACATCTGT ACTGACAACG

TGAAGACAGG CATTGCAAAC ACACTGGGGA ACAAGGGAGC

CGTGGGGGTG TCGTTCATGT TCAATGGAAC CTCCTTAGGG

TTCGTCAACA GCCACTTGAC TTCAGGAAGT GAAAAGAAAC
```

```
TCAGGCGAAA CCAAAACTAT ATGAACATTC TCCGGTTCCT
GGCCCTGGGC GACAAGAAGC TGAGTCCCTT AACATCACT
CACCGCTTCA CGCACCTCTT CTGGTTTGGG GATCTTAACT
ACCGTGTGGA TCTGCCTACC TGGGAGGCAG AAACCATCAT
CCAGAAAATC AAGCAGCAGC AGTACGCAGA CCTCCTGTCC
CACGACCAGC TGCTCACAGA GAGGAGGGAG CAGAAGGTCT
TCCTACACTT CGAGGAGGAA GAAATCACGT TTGCCCCAAC
CTACCGTTTT GAGAGACTGA CTCGGGACAA ATACGCCTAC
ACCAAGCAGA AAGCGACAGG GATGAAGTAC AACTTGCCTT
CCTGGTGTGA CCGAGTCCTC TGGAAGTCTT ATCCCCTGGT
GCACGTGGTG TGTCAGTCTT ATGGCAGTAC CAGCGACATC
ATGACGAGTG ACCACAGCCC TGTCTTTGCC ACATTTGAGG
CAGGAGTCAC TTCCCAGTTT GTCTCCAAGA ACGGTCCCGG
GACTGTTGAC AGCCAAGGAC AGATTGAGTT TCTCAGGTGC
TATGCCACAT TGAAGACCAA GTCCCAGACC AAATTCTACC
TGGAGTTCCA CTCGAGCTGC TTGGAGAGTT TTGTCAAGAG
TCAGGAAGGA GAAAATGAAG AAGGAAGTGA GGGGGAGCTG
GTGGTGAAGT TTGGTGAGAC TCTTCCAAAG CTGAAGCCCA
TTATCTCTGA CCCTGAGTAC CTGCTAGACC AGCACATCCT
CATCAGCATC AAGTCCTCTG ACAGCGACGA ATCCTATGGC
GAGGGCTGCA TTGCCCTTCG GTTAGAGGCC ACAGAAACGC
AGCTGCCCAT CTACACGCCT CTCACCCACC ATGGGGAGTT
GACAGGCCAC TTCCAGGGGG AGATCAAGCT GCAGACCTCT
CAGGGCAAGA CGAGGGAGAA GCTCTATGAC TTTGTGAAGA
CGGAGCGTGA TGAATCCAGT GGGCCAAAGA CCCTGAAGAG
CCTCACCAGC CACGACCCCA TGAAGCAGTG GGAAGTCACT
AGCAGGGCCC CTCCGTGCAG TGGCTCCAGC ATCACTGAAA
TCATCAACCC CAACTACATG GGAGTGGGGC CCTTTGGGCC
ACCAATGCCC CTGCACGTGA AGCAGACCTT GTCCCCTGAC
CAGCAGCCCA CAGCCTGGAG CTACGACCAG CCGCCCAAGG
ACTCCCCGCT GGGGCCCTGC AGGGGAGAAA GTCCTCCGAC
ACCTCCCGGC CAGCCGCCCA TATCACCCAA GAAGTTTTTA
CCCTCAACAG CAAACCGGGG TCTCCCTCCC AGGACACAGG
AGTCAAGGCC CAGTGACCTG GGGAAGAACG CAGGGGACAC
GCTGCCTCAG GAGGACCTGC CGCTGACGAA GCCCGAGATG
TTTGAGAACC CCCTGTATGG GTCCCTGAGT TCCTTCCCTA
AGCCTGCTCC CAGGAAGGAC CAGGAATCCC CCAAAATGCC
GCGGAAGGAA CCCCCGCCCT GCCCGGAACC CGGCATCTTG
TCGCCCAGCA TCGTGCTCAC CAAAGCCCAG GAGGCTGATC
GCGGCGAGGG GCCCGGCAAG CAGGTGCCCG CGCCCCGGCT
GCGCTCCTTC ACGTGCTCAT CCTCTGCCGA GGGCAGGGCG
GCCGGCGGGG ACAAGAGCCA AGGGAAGCCC AAGACCCCGG
TCAGCTCCCA GGCCCCGGTG CCGGCCAAGA GGCCCATCAA
GCCTTCCAGA TCGGAAATCA ACCAGCAGAC CCCGCCCACC
CCGACGCCGC GGCCGCCGCT GCCAGTCAAG AGCCCGGCGG
TGCTGCACCT CCAGCACTCC AAGGGCCGCG ACTACCGCGA
CAACACCGAG CTCCCGCATC ACGGCAAGCA CCGGCCGGAG
GAGGGGCCAC CAGGGCCTCT AGGCAGGACT GCCATGCAGT
GAAGCCCTCA GTGAGCTGCC ACTGAGTCGG GAGCCCAGAG
GAACGGCGTG AAGCCACTGG ACCCTCTCCC GGGACCTCCT
GCTGGCTCCT CCTGCCCAGC TTCCTATGCA AGGCTTTGTG
TTTTCAGGAA AGGGCCTAGC TTCTGTGTGG CCCACAGAGT
TCACTGCCTG TGAGACTTAG CACCAAGTGC TGAGGCTGGA
AGAAAAACGC ACACCAGACG GGCAACAAAC AGTCTGGGTC
CCCAGCTCGC TCTTGGTACT TGGGACCCCA GTGCCTCGTT
GAGGGCGCCA TTCTGAAGAA AGGAACTGCA GCGCCGATTT
GAGGGTGGAG ATATAGATAA TAATAATATT AATAATAATA
ATGGCCACAT GGATCGAACA CTCATGATGT GCCAAGTGCT
GTGCTAAGTG CTTTACGAAC ATTCGTCATA TCAGGATGAC
CTCGAGAGCT GAGGCTCTAG CCACCTAAAA CCACGTGCCC
AAACCCACCA GTTTAAAACG GTGTGTGTTC GGAGGGGTGA
AAGCATTAAG AAGCCCAGTG CCCTCCTGGA GTGAGACAAG
GGCTCGGCCT TAAGGAGCTG AAGAGTCTGG GTAGCTTGTT
TAGGGTACAA GAAGCCTGTT CTGTCCAGCT TCAGTGACAC
AAGCTGCTTT AGCTAAAGTC CCGCGGGTTC CGGCATGGCT
AGGCTGAGAG CAGGGATCTA CCTGGCTTCT CAGTTCTTTG
GTTGGAAGGA GCAGGAAATC AGCTCCTATT CTCCAGTGGA
GAGATCTGGC CTCAGCTTGG GCTAGAGATG CCAAGGCCTG
TGCCAGGTTC CCTGTGCCCT CCTCGAGGTG GGCAGCCATC
ACCAGCCACA GTTAAGCCAA GCCCCCCAAC ATGTATTCCA
TCGTGCTGGT AGAAGAGTCT TTGCTGTTGC TCCCGAAAGC
CGTGCTCTCC AGCCTGGCTG CCAGGGAGGG TGGGCCTCTT
GGTTCCAGGC TCTTGAAATA GTGCAGCCTT TTCTTCCTAT
CTCTGTGGCT TTCAGCTCTG CTTCCTTGGT TATTAGGAGA
ATAGATGGGT GATGTCTTTC CTTATGTTGC TTTTTCAACA
TAGCAGAATT AATGTAGGGA GCTAAATCCA GTGGTGTGTG
TGAATGCAGA AGGGAATGCA CCCCACATTC CCATGATGGA
AGTCTGCGTA ACCAATAAAT TGTGCCTTTC TCACTCAAAA
AAAAAAAAAA AAAA
```

The amino acid sequence of INNP5D is shown as SEQ ID NO: 5 below.

MVPCWNHGNITRSKAEELLSRTGKDGSFLVRASESISRAYALCVLYRNCV
YTYRILPNEDDKFTVQASEGVSMRFFTKLDQLIEFYKKENMGLVTHLQYP
VPLEEEDTGDDPEEDTVESVVSPPELPPRNIPLTASSCEAKEVPFSNENP
RATETSRPSLSETLFQRLQSMDTSGLPEEHLKAIQDYLSTQLAQDSEFVK
TGSSSLPHLKKLTTLLCKELYGEVIRTLPSLESLQRLFDQQLSPGLRPRP
QVPGEANPINMVSKLSQLTSLLSSIEDKVKALLHEGPESPHRPSLIPPVT
FEVKAESLGIPQKMQLKVDVESGKLIIKKSKDGSEDKFYSHKKILQLIKS
QKFLNKLVILVETEKEKILRKEYVFADSKKREGFCQLLQQMKNKHSEQPE
PDMITIFIGTWNMGNAPPPKKITSWFLSKGQGKTRDDSADYIPHDIYVIG
TQEDPLSEKEWLEILKHSLQEITSVTFKTVAIHTLWNIRIVVLAKPEHEN
RISHICTDNVKTGIANTLGNKGAVGVSFMFNGTSLGFVNSHLTSGSEKKL
RRNQNYMNILRFLALGDKKLSPFNITHRFTHLFWFGDLNYRVDLPTWEAE
TIIQKIKQQQYADLLSHDQLLTERREQKVFLHFEEEEITFAPTYRFERLT
RDKYAYTKQKATGMKYNLPSWCDRVLWKSYPLVHVVCQSYGSTSDIMTSD
HSPVFATFEAGVTSQFVSKNGPGTVDSQGQIEFLRCYATLKTKSQTKFYL
EFHSSCLESFVKSQEGENEEGSEGELVVKFGETLPKLKPIISDPEYLLDQ
HILISIKSSDSDESYGEGCIALRLEATETQLPIYTPLTHHGELTGHFQGE
IKLQTSQGKTREKLYDFVKTERDESSGPKTLKSLTSHDPMKQWEVTSRAP
PCSGSSITEIINPNYMGVGPFGPPMPLHVKQTLSPDQQPTAWSYDQPPKD
SPLGPCRGESPPTPPGQPPISPKKFLPSTANRGLPPRTQESRPSDLGKNA
GDTLPQEDLPLTKPEMFENPLYGSLSSFPKPAPRKDQESPKMPRKEPPPC
PEPGILSPSIVLTKAQEADRGEGPGKQVPAPRLRSFTCSSSAEGRAAGGD
KSQGKPKTPVSSQAPVPAKRPIKPSRSEINQQTPPTPTPRPPLPVKSPAV
LHLQHSKGRDYRDNTELPHHGKHRPEEGPPGPLGRTAMQ

The complete nucleotide sequence of ATG16L1 is shown as SEQ ID NO: 6 below.

```
ACTAGCGAGC GCCCTGCGTA GGCACCGGCT CCTGAGCCCG
TGCTTCGGGT GAGGGGGCGG GTCTTCCGGC CCTCTCGAAA
ATCATTTCCG GCATGAGCCG AAGACCGTC CCGGATGGCC
TCGGGGACTG CCAGTGTGTG GAGGTGAGCT CCGGGATTGC
CGGCATTCCC GCTTCTGCTG GTTGCTCAT GCTGCAGGCT
GCGGCCGTCA GCCCTCGCTC GCATTGGTGG CGCTGAGGTG
CCGGGGCAGC AAGTGACATG TCGTCGGGCC TCCGCGCCGC
TGACTTCCCC CGCTGGAAGC GCCACATCTC GGAGCAACTG
AGGCGCCGGG ACCGGCTGCA GAGACAGGCG TTCGAGGAGA
TCATCCTGCA GTATAACAAA TTGCTGGAAA AGTCAGATCT
TCATTCAGTG TTGGCCCAGA AACTACAGGC TGAAAAGCAT
GACGTACCAA ACAGGCACGA GATAAGTCCC GGACATGATG
GCACATGGAA TGACAATCAG CTACAAGAAA TGGCCCAACT
GAGGATTAAG CACCAAGAGG AACTGACTGA ATTACACAAG
```

```
AAACGTGGGG AGCTCAACTG GTGATTGACC TGAATAACCA
AATGCAGCGG AAGGACAGGG AGATGCAGAT GAATGAAGCA
AAAATTGCAG AATGTTTGCA GACTATCTCT GACCTGGAGA
CGGAGTGCCT AGACCTGCGC ACTAAGCTTT GTGACCTTGA
AAGAGCCAAC CAGACCCTGA AGGATGAATA TGATGCCCTG
CAGATCACTT TTACTGCCTT GGAGGGAAAA CTGAGGAAAA
CTACGGAAGA GAACCAGGAG CTGGTCACCA GATGGATGGC
TGAGAAAGCC CAGGAAGCCA ATCGGCTTAA TGCAGAGAAT
GAAAAAGACT CCAGGAGGCG GCAAGCCCGG CTGCAGAAAG
AGCTTGCAGA AGCAGCAAAG GAACCTCTAC CAGTCGAACA
GGATGATGAC ATTGAGGTCA TTGTGGATGA AACTTCTGAT
CACACAGAAG AGACCTCTCC TGTGCGAGCC ATCAGCAGAG
CAGCCACTAA GCGACTCTCG CAGCCTGCTG GAGGCCTTCT
GGATTCTATC ACTAATATCT TGGGAGACG CTCTGTCTCT
TCCTTCCCAG TCCCCCAGGA CAATGTGGAT ACTCATCCTG
GTTCTGGTAA AGAAGTGAGG GTACCAGCTA CTGCCTTGTG
TGTCTTCGAT GCACATGATG GGGAAGTCAA CGCTGTGCAG
TTCAGTCCAG GTTCCCGGTT ACTGGCCACT GGAGGCATGG
ACCGCAGGGT TAAGCTTTGG GAAGTATTTG GAGAAAAATG
TGAGTTCAAG GGTTCCCTAT CTGGCAGTAA TGCAGGAATT
ACAAGCATTG AATTTGATAG TGCTGGATCT TACCTCTTAG
CAGCTTCAAA TGATTTTGCA AGCCGAATCT GGACTGTGGA
TGATTATCGA TTACGGCACA CACTCACGGG ACACAGTGGG
AAAGTGCTGT CTGCTAAGTT CCTGCTGGAC AATGCGCGGA
TTGTCTCAGG AAGTCACGAC CGGACTCTCA AACTCTGGGA
TCTACGCAGC AAAGTCTGCA TAAAGACAGT GTTTGCAGGA
TCCAGTTGCA ATGATATTGT CTGCACAGAG CAATGTGTAA
TGAGTGGACA TTTTGACAAG AAAATTCGTT TCTGGGACAT
TCGATCAGAG AGCATAGTTC GAGAGATGGA GCTGTTGGGA
AAGATTACTG CCCTGGACTT AAACCCAGAA AGGACTGAGC
TCCTGAGCTG CTCCCGTGAT GACTTGCTAA AAGTTATTGA
TCTCCGAACA AATGCTATCA AGCAGACATT CAGTGCACCT
GGGTTCAAGT GCGGCTCTGA CTGGACCAGA GTTGTCTTCA
GCCCTGATGG CAGTTACGTG GCGGCAGGCT CTGCTGAGGG
CTCTCTGTAT ATCTGGAGTG TGCTCACAGG GAAAGTGGAA
AAGGTTCTTT CAAAGCAGCA CAGCTCATCC ATCAATGCGG
TGGCGTGGTC GCCCTCTGGC TCGCACGTTG TCAGTGTGGA
CAAAGGATGC AAAGCTGTGC TGTGGGCACA GTACTGACGG
GGCTCTCAGG GCTGGGAGGA CCCCAGTGCC CTCCCTCAGAA
GAAGCACATG GGCTCCTGCA GCCCTGTCCT GGCAGGTGAT
GTGCTGGGTA TAGCATGGAC CTCCCAGAGA AGCTCAAGCT
```

```
ATGTGGCACT GTAGCTTTGC CGTGAATGGG ATTTCTGAAG

ATTTGACTGA GGTCTCTCTT GGCCTGGAAG AATAACACTG

AAAAAACCTG ACGCTGCGGT CACTTAGCAG AGGCTCAGGT

TCTTGCCTTG GGAAACACTA CTAGCTCTGA CCTTCCATAC

CTCACTTGGG GGAGCACAGG GCCCGCTGG GCCTCCTCAC

CAACGGCAGT GCCAAAATCA GCCCCCACAT CAAGGTGGTG

TTCTCTGTGC TTTCTCTCGT CCTTCCAAAG TCGGTTCTGG

CCTAACGCAT GTCCCAACAC CTTGGGTTCA TTTGCCCGGT

GAACTCACTT TAAGCATTGG ATTAACGGAA ACTCCCGAAC

TACAGACCCC TCCCTGGTGG GTTGCATGAA TGTGTCTCAT

TACTGCTGAA ATGTCCTCAC ATCTCTTTCA CTGTTCTTCA

GAGCTTTCTG GCTCTCTTTC CCCCACAAAA TTCGACATAT

TTAAAAATCT CCGTGTGGCT TTAAAAAATG GTTTTTTGTT

TTTTTGTTTT TTTGAGGTGG GAGAGGATGT GTGAAAATCT

TTTCCAGGGA AATGGGTTCG CTGCAGAGGT AAGGATGTGT

TCCTGTATCG ATCTGCAGAC ACCCAGAAGG TGGGTGCACA

CTGCATGCTT GGGGGTGCCA AGGGATTCGA GACCTCCAAC

ATACTTGTCT GAAGGTGGTG ATTCTGGCCA TGGCCCCTCT

GCCAAGCCTG TGTGCGATGC CCTTGGTGCT TTAGTGCAAG

AAGCCTAGGC TCAGAAGCAC AGCAGCGCCA TCTTTCCGTT

TCAGGGGTTG TGATGAAGGC CAAGGAAAAA CATTTATCTT

TACTATTTTA CCTACGTATA AAGTTTTAGT TCATTGGGTG

TGCGAAACAC CCTTTTTATC ACTTTTAAAT TTGCACTTTA

TTTTTTTTCT TCCATGCTTG TTCTCTGGAC ATTTGGGGAT

GTGAGTGTTA GAGCTGGTGA GAGAGGAGTC AGGTGGCCTT

CCCACCGATG GTCCTGGCCT CCACCTGCCC TCTCTTCCCT

GCCTGATCAC CGCTTTCCAA TTTGCCCTTC AGAGAACTTA

AGTCAAGGAG AGTTGAAATT CACAGGCCAG GGCACATCTT

TTATTTATTT CATTATGTTG GCCAACAGAA CTTGATTGTA

AATAATAATA AAGAAATCTG TTATATACTT TTCAAACTCC

AAAAAAA
```

The amino acid sequence of ATG16L1 is shown as SEQ ID NO: 7 below.

```
MQRKDREMQMNEAKIAECLQTISDLETECLDLRTKLCDLERANQTLKDEY

DALQITFTALEGKLRKTTEENQELVTRWMAEKAQEANRLNAENEKDSRRR

QARLQKELAEAAKEPLPVEQDDDIEVIVDETSDHTEETSPVRAISRAATK

RLSQPAGGLLDSITNIFGRRSVSSFPVPQDNVDTHPGSGKEVRVPATALC

VFDAHDGEVNAVQFSPGSRLLATGGMDRRVKLWEVFGEKCEFKGSLSGSN

AGITSIEFDSAGSYLLAASNDFASRIWTVDDYRLRHTLTGHSGKVLSAKF

LLDNARIVSGSHDRTLKLWDLRSKVCIKTVFAGSSCNDIVCTEQCVMSGH

FDKKIRFWDIRSESIVREMELLGKITALDLNPERTELLSCSRDDLLKVID

LRTNAIKQTFSAPGFKCGSDWTRVVFSPDGSYVAAGSAEGSLYIWSVLTG

KVEKVLSKQHSSSINAVAWSPSGSHVVSVDKGCKAVLWAQY
```

As used herein, "protein" and "polypeptide" are used synonymously to mean any peptide-linked chain of amino acids, regardless of length or post-translational modification, e.g., glycosylation or phosphorylation.

The term "gene" is meant to be a nucleic acid molecule that codes for a particular protein, or in certain cases, a functional or structural RNA molecule.

As used herein, the terms "detect", "detecting", or "detection" may describe either the general act of discovering or discerning or the specific observation of a detectably labeled composition.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a mammalian (e.g., human) subject, including, but not limited to, humans, non-human primates, rodents, and the like, to be treated, diagnosed, and/or to obtain a biological sample from.

As used herein, "bind," "binds,", "binding", or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and non-covalent (hydrogen bonding, hydrophobic, ionic, and van der waals).

The term "labeled," with regard to a cell, probe or antibody, is intended to encompass direct labeling of the cell, probe or antibody by coupling (i.e., physically linking) a detectable substance to the cell, probe, or antibody.

When referring to a nucleic acid molecule or polypeptide, the term "native" refers to a naturally-occurring (e.g., a WT or wild type) nucleic acid or polypeptide.

As used herein, the terms "diagnostic," "diagnose" and "diagnosed" mean identifying the presence or nature of a pathologic condition.

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, and the like. Examples of samples include saliva, serum, breast tissue, and blood. As used herein, the terms "treatment" and "therapy" are defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-S'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target. When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above. As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tln of the formed hybrid, and the G:C ratio within the nucleic acids. A single molecule that contains pairing of complementary nucleic acids within its structure is said to be "self-hybridized."

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an agent, preferably a detectably labeled agent, capable of forming a complex with a target molecule immobilized or pre-coated on a surface. Where the target molecule is a polynucleotide, the probe is another polynucleotide, a nucleic acid specific binding protein or antibody, or other nucleic acid binding molecule. For example, the probe is another polynucleotide such as RNA or DNA or a peptide nucleic acid (PNA, nucleic acid having a peptide backbone). Where the target molecule is a protein, such as a ligand, a receptor, an antibody, cell surface protein, and the like, the probe is, for example, a receptor, ligand, antibody, polynucleotide, or other biopolymer or smaller molecule capable of forming a complex with the target protein. For the purposes of the present disclosure, the term "probe" will be used to refer to a labeled molecule capable of forming a complex with an immobilized molecule (the "target" as used herein) on a support surface or substrate. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids include nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells, and the polypeptides are purified by the removal of host cell proteins; the percent of recombinant polypeptides is thereby increased in the sample.

Although kits, assays, and methods similar or equivalent to those described herein can be used in the practice or testing of the present invention, suitable kits, assays, and methods are described below. All publications, patent applications, and patents mentioned herein are incorporated by reference in their entirety. In the case of conflict, the present specification, including definitions, will control. The particular embodiments discussed below are illustrative only and not intended to be limiting.

The present invention provides DNA and RNA based diagnostic methods that either directly or indirectly detect the INPP5D-ATG16L1 fusion mRNA and protein variants. The present invention also provides compositions and kits for diagnostic purposes. The diagnostic methods of the present invention may be qualitative or quantitative.

The analysis of RNA in a sample for the presence of the INPP5D-ATG16L1 fusion mRNA specific polynucleotide sequences (e.g., an mRNA having the sequence set forth in SEQ ID NO: 3 or a transcript variant thereof, or a portion of the INPP5D-ATG16L1 fusion mRNA incorporating at least some nucleotides on either side of the fusion point [i.e., nucleotides from both INPP5D exon 25 and ATG16L1 exon 2]) found in a patient's biological sample according to the present invention may be performed using blood.

In an embodiment, the method includes the steps of obtaining a biological sample from a subject and analyzing the biological sample for the presence of the INPP5D-ATG16L1 fusion mRNA.

In an embodiment, the method includes the steps of obtaining a biological sample from a subject and analyzing the biological sample for the presence of the INPP5D-ATG16L1 fusion protein.

In one embodiment, the detection of the INPP5D-ATG16L1 fusion mRNA transcript or polypeptide identifies the subject as having IBD or Crohn's Disease.

In an embodiment, the method includes the steps of obtaining a biological sample from a subject and analyzing the biological sample for the presence of the INPP5D-ATG16L1 fusion mRNA, and if it is present, diagnosing the subject as having or being at risk of having a more severe form of IBD or Crohn's Disease.

In an embodiment, the method includes the steps of obtaining a biological sample from a subject and analyzing the biological sample for the presence of the INPP5D-ATG16L1 fusion protein, and if it is present, diagnosing the subject as having or being at risk of having a more severe form of IBD or Crohn's Disease.

In an embodiment, the method includes the steps of obtaining a biological sample from a subject and analyzing the biological sample for the presence of the INPP5D-ATG16L1 fusion mRNA, and if it is present, diagnosing the subject as having or being at risk of having a more severe form of IBD or Crohn's Disease and prescribing an appropriate treatment.

In an embodiment, the method includes the steps of obtaining a biological sample from a subject and analyzing the biological sample for the presence of the INPP5D-ATG16L1 fusion protein, and if it is present, diagnosing the subject as having or being at risk of having a more severe form of IBD or Crohn's Disease and prescribing an appropriate treatment.

Quantitative diagnostic methods may be used, for example, to discriminate between indolent and aggressive IBD or Crohn's Disease via a cutoff or threshold level. Where applicable, qualitative or quantitative diagnostic methods may also include amplification of target, signal or intermediary (e.g., a universal primer). An initial assay may confirm the presence of INPP5D-ATG16L1 fusion mRNA variants but not identify the specific transcript variant. A secondary assay is then performed to determine the identity of the particular transcript variant, if desired. The second assay may use a different detection technology than the initial assay. The diagnostic methods of the present invention may also be modified with reference to data correlating a particular INPP5D-ATG16L1 fusion mRNA variant with the stage, aggressiveness or progression of the IBD or Crohn's Disease. Ultimately, the information provided by the methods of the present invention will assist a physician in diagnosing and choosing the best course of treatment for a particular patient. The INPP5D-ATG16L1 fusion mRNA variants may be detected along with other markers in a multiplex or panel format. Markers are selected for their predictive value alone or in combination with the INPP5D-ATG16L1 fusion mRNA variants.

The first steps of practicing this invention are to obtain a biological sample from a test subject and extract mRNA from the sample. Any patient sample suspected of containing the INPP5D-ATG16L1 fusion mRNA variants may be tested according to the methods of the present invention. The isolation of biological samples from a subject which contain nucleic acids is well known in the art. The biological sample can be sputum, blood, a blood fraction, tissue or fine needle biopsy sample, urine, stool, peritoneal fluid, or pleural fluid. Preferably, the biological sample is blood or a tissue sample from the gut, such as those obtained during an endoscopic procedure, such as those for diagnosing UC or CD. Biological samples, such as blood samples or biopsies, may be taken from appropriate anatomic sites or tissues utilizing standard techniques routinely employed in medical clinics and hospitals. For example, a blood or an intestinal tissue sample is obtained from a person to be tested for the INPP5D-ATG16L1 fusion mRNA using a method of the present invention. Collection of a blood or tissue sample, e.g., an intestinal tissue sample, from an individual is performed in accordance with the standard protocol hospitals or clinics generally follow, such as during a blood drawing, biopsy, or surgical procedure. An appropriate amount of blood or tissue sample is collected and may be stored according to standard procedures prior to further preparation.

The patient sample typically requires preliminary processing designed to isolate or enrich the sample for the INPP5D-ATG16L1 fusion mRNA variants or cells that contain the INPP5D-ATG16L1 fusion mRNA variants. A variety of techniques known to those of ordinary skill in the art may be used for this purpose, including but not limited to: centrifugation; immunocapture; cell lysis; and, nucleic acid target capture; all of which are described in EP Pat. No. 1 409 727, which is hereby incorporated by reference in its entirety.

The INPP5D-ATG16L1 fusion mRNA variants may be detected using a variety of nucleic acid techniques known to those of ordinary skill in the art, including but not limited to: nucleic acid sequencing; nucleic acid hybridization; and, nucleic acid amplification. There are numerous methods for extracting mRNA from a biological sample. The general methods of mRNA preparation (e.g., described by Sambrook and Russell, Molecular Cloning: A Laboratory Manual 3d ed., 2001, which is hereby incorporated by reference in its entirety) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack, experimental RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer when scanned from the top of the gel to the bottom. Dye terminator sequencing alternatively labels the terminators. Complete sequencing can be performed in a single reaction by labeling each of the di-deoxynucleotide chain-terminators with a separate fluorescent dye, which fluoresces at a different wavelength.

In one embodiment, a fusion mRNA transcript is detected by contacting a biological sample with reagents using an hybridization assay.

Illustrative non-limiting examples of nucleic acid hybridization techniques include, but are not limited to, in situ hybridization (ISH), microarray, and Southern or Northern blot.

Single probes for detecting the INPP5D-ATG16L1 fusion mRNA must target both the 3' end of exon 25 of INPP5D and the 5' end of exon 2 of ATG16L1 (i.e., the nucleotides of the INPP5D-ATG16L1 fusion mRNA corresponding to exon 25 of INPP5D and exon 2 of ATG16L1), with nucleotides complementary to the transcribed nucleotides. Probes can be of any length (i.e., number of nucleotides) necessary to obtain the specificity desired, which, in some cases, can be as short as 8-12, but is preferably at least 15 nucleotides long. Although theoretically the probe could identify the INPP5D-ATG16L1 fusion mRNA if only one of the nucleotides in the probe targeted a nucleotide of a first exon (for example, exon 2 of ATG16L1) and the rest of the nucleotides targeted nucleotides of a second exon (e.g., exon 25 of INPP5D), it is preferable that, regardless of the length of the probe, the probe target a minimum of 5 or 6 nucleotides from each of exons 25 and 2, and more preferably, a minimum of 9-11 nucleotides from each exon. The longer the probe, and the more nucleotides from each exon it targets, the more specific it will be. However, since there may be problems if the melting temperature ($T_m$) of the probe (or a primer) gets too high or if the probe gets too long, it is preferable to use probes of the minimum length necessary to target the INPP5D-ATG16L1 fusion mRNA with high specificity. Unless highly repetitive elements are in the sequence being targeted, it has been found, for example purposes only, that a 20-mer sequence minimum for DNA, and a 19-mer minimum for RNA and cDNA, work well.

For detection methodologies which may use multiple probes, such as FRET, the probe design is similar. As there is more flexibility in choice of target sequence as the target can be shifted somewhat without affecting detection sensitivity significantly, it is preferred that each of the multiple probes target an invariant or conserved region. In the absence of a conserved region on each exon, multiple versions of each probe (e.g., acceptor labeled probe and donor labeled probe) may be necessary, such that each target a specific variant.

There may be individual variations in the transcripts of the exons due to variations in the genetic sequence for the INPP5D and/or ATG16L1 genes, and some of these variations may be located close enough to the 3' end of exon 25 or the 5' end of exon 2 to affect probe design (e.g., within 10 nucleotides). It is therefore preferred that the probe target invariant or conserved sequences flanking the fusion. In a preferred embodiment, the probe for detecting the INPP5D-ATG16L1 fusion mRNA targets invariant or conserved regions of the 3' end of exon 25 of INPP5D and exon 2 of ATG16L1 flanking the fusion point. If there are variations in either the INPP5D or ATG16L1 within the 5 or 6 nucleotides flanking the fusion point, it may be necessary to have two or more probes to ensure detection of the INPP5D-ATG16L1 fusion mRNA, each designed for a specific variant.

In an embodiment, a biological sample from a subject is assayed for the presence of INPP5D-ATG16L1 fusion mRNA using a probe.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using autoradiography, fluorescence microscopy or immunohistochemistry, respectively. ISH can also use two or more probes, labeled with radioactivity or the other non-radioactive labels, to simultaneously detect two or more transcripts.

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies including, but not limited to: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In another embodiment, a fusion mRNA transcript is detected by contacting a biological sample with reagents using an amplification assay.

The INPP5D-ATG16L1 fusion mRNA variants may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990 which is hereby incorporated by reference in its entirety. The polymerase chain reaction (PCR) is described in detail in U.S. Pat. Nos. 4,683,195, 4,683,202, 4,800,159 and 4,965,188, each of which are hereby incorporated by reference in its entirety. Briefly, PCR uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol, 155: 335 (1987); and, Murakawa et al., DiVA 7: 287 (1988), each of which is hereby incorporated by reference in its entirety. Methods suitable for PCR amplification of ribonucleic acids are described by Romero and Rotbart in i Diagnostic Molecular Biology: Principles and Applications pp. 401-406; Persing et al., eds., Mayo Foundation, Rochester, Minn., 1993; Egger et al., *J. Clin. Microbiol.* 33:1442-1447, 1995; and U.S. Pat. No. 5,075,212, all of which are hereby incorporated by reference in its entirety.

PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998, which is hereby incorporated by reference in its entirety.

Once RNA is extracted from a sample, the presence of INPP5D-ATG16L1 fusion mRNA specific polynucleotide sequence (e.g., an mRNA having the sequence set forth in SEQ ID NO: 3 or a transcript variant thereof, or a portion of the INPP5D-ATG16L1 fusion mRNA incorporating at least some nucleotides on either side of the fusion point [i.e., nucleotides from both INPP5D exon 25 and ATG16L1 exon 2]) may be detected and the amount quantified. A method for detecting and/or quantifying the RNA is an amplification-based method, e.g., by polymerase chain reaction (PCR), especially reverse transcription-polymerase chain reaction (RT-PCR).

Another way to utilize PCR would be to exploit FRET between a donor label on the end of one primer and an acceptor molecule on an internal probe, or with a quenched fluorescent molecule in a 'classic' TaqMan assay. These various PCR-based methods are described in Didenko, "DNA Probes Using Fluorescence Resonance Energy Transfer (FRET): Designs and Applications," Biotechniques 31(5): 1106-1121 (2001), which is hereby incorporated by reference in its entirety.

Transcription mediated amplification (TMA) is described in detail in U.S. Pat. Nos. 5,824,518, 5,480,784, 5,399,491, and 5,554,516, each of which is hereby incorporated by reference in its entirety. Briefly, TMA synthesizes multiple copies of a target nucleic acid sequence autocatalytically under conditions of substantially constant temperature, ionic strength, and pH in which multiple RNA copies of the target sequence autocatalytically generate additional copies. In a variation described in U.S. Publ. No. 20060046265, which is hereby incorporated by reference in its entirety, TMA optionally incorporates the use of blocking moieties, terminating moieties, and other modifying moieties to improve TMA process sensitivity and accuracy. The ligase chain reaction (LCR) is described in Weiss, R., Science 254: 1292 (1991), which is hereby incorporated by reference in its entirety.

Briefly, LCR uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (SDA) is described in Walker et al., Proc. Natl. Acad. Sci USA 89:392-396 (1992); U.S. Pat. Nos. 5,270,184 and 5,455,166, each of which is hereby incorporated by reference in its entirety. Briefly, SDA uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315, which is hereby incorporated by reference in its entirety). Other amplification methods include, for example, nucleic acid sequence based amplification.

Other amplification methods include, for example: nucleic acid sequence based amplification (NASBA) described in U.S. Pat. No. 5,130,238, which is hereby incorporated by reference in its entirety; Q-beta replicase which uses an RNA replicase to amplify the probe molecule itself as described in Lizardi et al., BioTechnol 6:1197 (1988), which is hereby incorporated by reference in its entirety; transcription based amplification method described in Kwoh et al., Proc. Natl. Acad. Sci. USA 86:1173 (1989), which is hereby incorporated by reference in its entirety; and, self-sustained sequence replication described in Guatelli et al., Proc. Natl. Acad. Sci. USA 87:1874 (1990), which is hereby incorporated by reference in its entirety. For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)), which is hereby incorporated by reference in its entirety.

Non-amplified or amplified INPP5D-ATG16L1 fusion mRNA variants can be detected by any conventional means. For example, the INPP5D-ATG16L1 fusion mRNA variants can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. HPA is described in U.S. Pat. No. 5,283,174 and Norman C. Nelson et al., Nonisotopic Probing, Blotting, and Sequencing, ch. 17 (Larry J. Kricka ed., 2d ed. 1995), which is hereby incorporated by reference in its entirety.

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is hereby incorporated by reference in its entirety. Another method for determining the quantity of target sequence initially present in a sample, but which is not based on a real-time amplification, is disclosed in U.S. Pat. No. 5,710,029, which is hereby incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In one embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, which is hereby incorporated by reference in its entirety.

Another example of a detection probe having self-complementarity is a "molecular beacon". Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, each of which is hereby incorporated by reference in its entirety.

Other self-hybridizing probes are well known to those of ordinary skill in the art. By way of non-limiting example, probe binding pairs having interacting labels, such as those disclosed in U.S. Pat. No. 5,928,862, which is hereby incorporated by reference in its entirety, might be adapted for use in the present invention. Probe systems used to detect single nucleotide polymorphisms (SNPs) might also be utilized in the present invention. Additional detection systems include "molecular switches," as disclosed in U.S. Publ. No. 20050042638, which is hereby incorporated by reference in its entirety. Other probes, such as those comprising intercalating dyes and/or fluorochromes, are also useful for detection of amplification products in the present invention and are described in U.S. Pat. No. 5,814,447, which is hereby incorporated by reference in its entirety In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject. The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of IBD being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

Compositions for use in the diagnostic methods of the present invention include, but are not limited to, amplification oligonucleotides and probes. Any of these compositions, alone or in combination with other compositions of the present invention, may be provided in the form of a kit. For example, a pair of amplification oligonucleotides and a detection probe may be provided in a kit for the amplification and detection of the INPP5D-ATG16L1 fusion mRNA variants. Kits may further comprise appropriate controls and/or detection reagents. The following examples are provided in order to demonstrate and further illustrate certain preferred embodiments and aspects of the present invention and are not to be construed as limiting the scope thereof.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; The Condensed Protocols From Molecular Cloning: A Laboratory Manual, by Joseph Sambrook et al., Cold Spring Harbor Laboratory Press, Cold Spring Harbor, N.Y., 2006; and Current Protocols in Molecular Biology, ed. Ausubel et al., Greene Publishing and Wiley-Interscience, New York, 1995 (with periodic updates), each of which is hereby incorporated by reference in its entirety. Immunology techniques are generally known in the art and are described in detail in methodology treatises such as Advances in Immunology, volume 93, ed. Frederick W. Alt, Academic Press, Burlington, Mass., 2007; Making and Using Antibodies: A Practical Handbook, eds. Gary C. Howard and Matthew R. Kaser, CRC Press, Boca Raton, Fl, 2006; Medical Immunology, 6$^{th}$ ed., edited by Gabriel Virella, Informa Healthcare Press, London, England, 2007; and Harlow and Lane ANTIBODIES: A Laboratory Manual, Cold Spring Harbor Laboratory Press, Cold Spring Harbor, N.Y., 1988, each of which is hereby incorporated by reference in its entirety.

In one embodiment, detection of the fusion mRNA transcript or polypeptide encoded by the fusion mRNA transcript comprises detecting the level of the fusion mRNA transcript or polypeptide encoded by the fusion mRNA transcript. The levels of INPP5D-ATG16L1 fusion mRNA transcript and protein can be measured by any means known to those skilled in the art. In the present invention, it is generally preferred to use antibodies, or antibody equivalents, to detect levels of biomarker protein. However, other methods for detection of biomarker expression can also be used. For example, INPP5D-ATG16L1 mRNA levels may be monitored by analysis of mRNA transcripts. Measuring INPP5D-ATG16L1 mRNA may be preferred, for example when the biological sample is a tumor, or tissue sample.

Methods for assessing levels of mRNA are well known to those skilled in the art. For example, detection of RNA transcripts may be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, which is hereby incorporated by reference in its entirety, or reverse transcribe mRNA into cDNA followed by symmetric gap ligase chain reaction (RT-AGLCR) as described by R. L. Marshall, et al., PCR Methods and Applications 4: 80-84 (1994), which is hereby incorporated by reference in its entirety. One suitable method for detecting INPP5D-ATG16L1 mRNA transcripts is described in reference Pabic et. al., *Hepatology,* 37(5): 1056-1066 (2003), which is hereby incorporated by reference in its entirety.

Other known amplification methods which can be utilized herein include but are not limited to the so-called "NASBA" or "3 SR" technique described in PNAS USA 87:1874-1878 (1990), which is hereby incorporated by reference in its entirety, and also described in *Nature* 350(6313):91-92 (1991), which is hereby incorporated by reference in its entirety; Q-beta amplification as described in published European Patent Application (EPA) No. 454-4610, which is hereby incorporated by reference in its entirety; strand displacement amplification (as described in Walker et al., *Clin. Chem.* 42:9-13 (1996) and European Patent Application No. 684315, each of which is hereby incorporated by reference in its entirety; and target mediated amplification, as described by PCT Publication WO 9322461, which is hereby incorporated by reference in its entirety.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Oligonucleotides corresponding to INPP5D-ATG16L1 nucleotide sequence are immobilized on a chip which is then hybridized with labeled nucleic acids of a test sample obtained from a patient. Positive hybridization signal is obtained with the sample containing INPP5D-ATG16L1 mRNA. Methods of preparing DNA arrays and their use are well known in the art. (See, for example, U.S. Pat. Nos. 6,618,679; 6,379,897; 6,664, 377; 6,451,536; 548,257; U.S. 20030157485 and Schena et al., *Science* 20:467-470 (1995); Gerhold et al., *Trends in Biochem. Sci.* 24:168-173 (1999); and Lennon et al., *Drug discovery Today* 5:59-65 (2000), which are hereby incorporated by reference in their entirety). Serial Analysis of Gene Expression (SAGE) can also be performed (See, for example, U.S. Patent Application 20030215858, which is hereby incorporated by reference in its entirety). In one embodiment, a first probe capable of binding to a first region of the INPP5D-ATG16L1 fusion mRNA encoding one of the two proteins ATG16L1 or INPP5D to capture it (for instance, a probe anchored to a substrate such as a chip or microarray) and a second labeled probe (e.g., such as labeled with a fluorophore) capable of binding to a second region of the INPP5D-ATG16L1 fusion mRNA encoding the other of the two proteins ATG16L1 or INPP5D can also be used to determine whether the INPP5D-ATG16L1 fusion mRNA is present and whether the subject should be diagnosed as having the INPP5D-ATG16L1 fusion mRNA. If an mRNA captured by the first probe is labeled by the second probe, the INPP5D-ATG16L1 fusion mRNA is present.

To monitor mRNA levels, for example, mRNA is extracted from the biological sample to be tested, reverse transcribed, and fluorescent-labeled cDNA probes are generated. The microarrays capable of hybridizing to INPP5D-ATG16L1 cDNA are then probed with the labeled cDNA probes, the slides scanned and fluorescence intensity measured. This intensity correlates with the hybridization intensity and expression levels.

INPP5D-ATG16L1 protein levels, or INPP5D-ATG16L1 activity, can also be measured, in particular, when the biological sample is a fluid sample such as blood or urine. In one embodiment, levels of INPP5D-ATG16L1 protein are measured by contacting the biological sample with an antibody-based binding moiety that specifically binds to INPP5D-ATG16L1, or to a fragment of INPP5D-ATG16L1. Formation of the antibody-INPP5D-ATG16L1 complex is then detected as a measure of INPP5D-ATG16L1 levels.

The predicted truncated SHIP1 protein (i.e., the INPP5D-ATG16L1 fusion protein) has not been detected to date in any of the patient PBMC (peripheral blood mononuclear cell) lysates that express the fusion mRNA. It is predicted that the truncated protein is unstable and is degraded by the cell and, thus, not expressed at the steady state. However, it may be that in some cases a INPP5D-ATG16L1 fusion protein can be detected. In an embodiment, the INPP5D-ATG16L1 fusion protein is targeted in the biological sample using an antibody raised against an epitope (sequence of amino acids) transcribed by the region of the fusion mRNA flanking the fusion point, the antibody optionally labeled for detection. After purification to separate out or concentrate the antibody and the proteins to which it is bound, detection is accomplished by detecting the antibody's label, or by comparing the size of the captured protein to the predicted size of the truncated SHIP1. In an embodiment, the INPP5D-ATG16L1 fusion protein is detected in a biological sample from a subject using an antibody raised against an epitope from the portion of the INPP5D protein transcribed and translated from its first 24 or 25 exons. After purification steps, the size of the captured protein is determined, such as by Western blot, and if it is sufficiently smaller than the 145 kDa size of the WT INPP5D (10%, 20%, 25%, 30%), or if it is approximately the 112 kDa size predicted for the truncated INPP5D protein (INPP5D-ATG16L1 fusion protein), the subject is diagnosed as having the INPP5D-ATG16L1 fusion mRNA.

The previously described detection technique can employ an antibody raised against the portion of the fusion protein transcribed by the region of the fusion mRNA encoding exons 2 through 18 of ATG16L1. After purification steps, if the size of the captured protein is sufficiently larger than 68 kDa or approximately 112 kDa in size, the subject is diagnosed as having the INPP5D-ATG16L1 fusion mRNA.

Whether the captured protein was transcribed by the INPP5D-ATG16L1 fusion mRNA can be determined using an antibody raised against a first portion of the fusion protein transcribed by a first region of the fusion mRNA encoding one of the two proteins (i.e., ATG16L1 or INPP5D) to capture the protein and an antibody raised against a second portion of the fusion protein transcribed by a second region of the fusion mRNA encoding the other of the two proteins (i.e., INPP5D or ATG16L1) to label the protein (e.g., with a fluorophore). If any captured protein are labeled, the subject is diagnosed as having the INPP5D-ATG16L1 fusion mRNA.

The term "antibody-based binding moiety" or "antibody" includes immunoglobulin molecules and immunologically active determinants of immunoglobulin molecules, e.g., molecules that contain an antigen binding site which specifically binds (immunoreacts with) to INPP5D-ATG16L1. The term "antibody-based binding moiety" is intended to include whole antibodies, e.g., of any isotype (IgG, IgA, IgM, IgE, etc), and includes fragments thereof which are also specifically reactive with INPP5D-ATG16L1 protein. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs, and single chain antibodies (scFv) containing a VL and VH domain joined by a peptide linker. The scFv's may be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule. In a preferred embodiment, the antibody-based binding moiety is detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the diagnostic and prognostic methods of the invention that use antibody based binding moieties for the detection of biomarker levels (e.g. INPP5D-ATG16L1), the level of biomarker present in the biological samples correlate to the intensity of the signal emitted from the detectably labeled antibody.

In one embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished via contacting a fusion mRNA polypetide encoded by the fusion mRNA transcript with reagents using any of a variety of other immunoassays. For example, by radioactively labeling an antibody, it is possible to detect the antibody through the use of radioimmune assays. The radioactive isotope can be detected by such means as the use of a gamma counter or a scintillation counter or by autoradiography. Isotopes which are particularly useful for the purpose of the present invention are $^3$H, $^{131}$I, $^{35}$S, $^{14}$C, and preferably $^{125}$I.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of INPP5D-ATG16L1 can be detected by immunoassays, such as enzyme linked immunoabsorbant assay (ELISA), radioimmunoassay (RIA), Immunoradiometric assay (IRMA), Western blotting, or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, each of which is hereby incorporated by reference in its entirety.

"Radioimmunoassay" is a technique for detecting and measuring the concentration of an antigen using a labeled (e.g. radioactively labeled) form of the antigen. Examples of radioactive labels for antigens include $^3$H, $^{14}$C, and $^{125}$I. The concentration of antigen INPP5D-ATG16L1 in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. *J. Clin. Chem. Clin. Biochem.* 22:895-904 (1984), each of which is hereby incorporated by reference in its entirety.

In a "sandwich ELISA", an antibody (e.g. anti-INPP5D-ATG16L1) is linked to a solid phase (i.e. a microtiter plate) and exposed to a biological sample containing antigen (e.g. INPP5D-ATG16L1). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (e.g. INPP5D-ATG16L1). The antigen-antibody mixture is then contacted with a solid phase (e.g. a microtiter plate) that is coated with antigen (i.e., INPP5D-ATG16L1). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta.-galactosidase), or chemical methods (e.g., DAB/Substrate chromagen).

Other techniques may be used to detect the biomarkers of the invention, according to a practitioner's preference, and based upon the present disclosure. One such technique is Western blotting (Towbin et al., *Proc. Nat. Acad. Sci.* 76:4350 (1979), which is hereby incorporated by reference in its entirety), wherein a suitably treated sample is run on an SDS-PAGE gel before being transferred to a solid support, such as a nitrocellulose filter. Detectably labeled antibodies that specifically bind to INPP5D-ATG16L1 can then be used to assess biomarker levels, where the intensity of the signal from the detectable label corresponds to the amount of biomarker present. Levels can be quantitated, for example by densitometry.

In addition, biomarkers of the invention may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are hereby incorporated by reference in their entirety.

Mass spectrometry methods are well known in the art and have been used to quantify and/or identify biomolecules, such as proteins (see, e.g., Li et al., *Tibtech* 18:151-160 (2000); Rowley et al., *Methods* 20: 383-397 (2000); and Kuster and Mann *Curr. Opin. Structural Biol.* 8: 393-400 (1998), each of which is hereby incorporated by reference in its entirety). Further, mass spectrometric techniques have been developed that permit at least partial de novo sequencing of isolated proteins (Chait et al., *Science* 262:89-92 (1993); Keough et al., *Proc. Natl. Acad. Sci. USA* 96:7131-6 (1999); Bergman, EXS 88:133-44 (2000), each of which is hereby incorporated by reference in its entirety.

In certain embodiments, a gas phase ion spectrophotometer is used. In other embodiments, laser-desorption/ionization mass spectrometry is used to analyze the sample.

Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. Nos. 5,118,937 and 5,045,694, each of which is hereby incorporated by reference in its entirety.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361, each of which is hereby incorporated by reference in its entirety. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, $4^{th}$ ed. Vol. 15 (John Wiley & Sons, New York 1995), pp. 1071-1094, each of which is hereby incorporated by reference in its entirety.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands that any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g., $^{13}C$) thereby permitting the test sample to mixed with the known control sample in the same mass spectrometry run.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one embodiment, biomarker levels are measured by MALDI-TOF mass spectrometry.

INPP5D-ATG16L1 levels can also be measured by using other biological assays, for example that measure activity, including but not limited to, zymography. Zymography is an assay well known to those skilled in the art and described in Heusen et al., *Anal. Biochem.,* 102:196-202 (1980); Wilson et al., *Journal of Urology* 149:653-658 (1993); Hernon et al., *J. Biol. Chem.* 261: 2814-2828 (1986); Braunhut et al., *J. Biol. Chem.* 269:13472-13479 (1994); and Moses et al., *Cancer Research* 58:1395-1399 (1998), which are hereby incorporated by reference in their entirety.

The antibodies for use in the present invention can be raised against INPP5D-ATG16L1, or a portion of the biomarker polypeptide. In a preferred embodiment, the antibody is raised against an antigen comprising a portion of the translated exon 25 of INPP5D and a portion of the translated exon 1 of ATG16L1. In a preferred embodiment, the antibody binds to portions of the INPP5D-ATG16L1 fusion protein corresponding to a INPP5D WT protein and a ATG16L1 WT protein. Methods useful for the production of INPP5D-ATG16L1 antibodies are disclosed in U.S. Application. Nos. 2002/0182702; 2003/0212256; 20020110894 and WO 01/11074, which are hereby incorporated by reference.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., *J. Immunology* 35: 1-21 (1990); and Kozbor et al., *Immunology Today* 4:72 (1983), each of which is hereby incorporated by reference in its entirety). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.), each of which is hereby incorporated by reference in its entirety, disclose bacteriophage display libraries and selection methods for producing antibody binding domain fragments.

The present invention is also directed to commercial kits for the diagnosis of IBD. The kit can be in any configuration well known to those of ordinary skill in the art and is useful for performing one or more of the methods described herein for the detection of INPP5D-ATG16L1. The kits are convenient in that they supply many if not all of the essential reagents for conducting an assay for the detection of INPP5D-ATG16L1 in a biological sample. In addition, the assay is preferably performed simultaneously with a standard or multiple standards that are included in the kit, such as a predetermined amount of INPP5D-ATG16L1 protein or nucleic acid, so that the results of the test can be quantitated or validated.

Another aspect of the present invention relates to a kit suitable for diagnosing IBD and/or Crohn's Disease. The kit includes one or more reagents suitable for detecting a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively.

In one embodiment, the reagents comprise oligonucleotide primers suitable for a nucleic acid amplification assay, oligonucleotide primers suitable for a hybridization assay, or antibodies or binding fragments thereof suitable for an immunoassay.

In one embodiment, the kit further comprises a substrate pre-coated with a probe. Probes suitable for use in the methods and kits of the present invention are described above. In one embodiment, the probe is an antibody, an oligonucleotide, or both.

In a further embodiment, the pre-coated substrate is an ELISA plate or a microarray. Microarrays suitable for use in the methods and kits of the present invention are described above. In one embodiment, the microarray is a DNA microarray or an antibody microarray.

Accordingly, the kits may include a means for detecting INPP5D-ATG16L1 levels such as antibodies, or antibody fragments, which selectively bind to INPP5D-ATG16L1 protein, or a set of DNA oligonucleotide primers that allows synthesis of cDNA encoding the protein, or for example, a DNA probe that detects expression of INPP5D-ATG16L1 mRNA. The diagnostic assay kit is preferentially formulated in a standard two-antibody binding format in which one INPP5D-ATG16L1-specific antibody captures INPP5D-ATG16L1 in a patient sample and another specific antibody is used to detect captured INPP5D-ATG16L1. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a calorimetric agent or radioisotope.

In one preferred embodiment, the kit comprises a means for detecting levels of INPP5D-ATG16L1 in a sample of urine. In a specific embodiment, the kit comprises a "dipstick" with anti-INPP5D-ATG16L1 antibodies or fragments, immobilized thereon, which specifically bind INPP5D-ATG16L1 protein. Specifically bound INPP5D-ATG16L1 protein can then be detected using, for example, a second antibody that is detectably labeled with a calorimetric agent or radioisotope.

In other embodiments, the assay kits may employ (but are not limited to) the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, and immunocytochemistry. For each kit the range, sensitivity, precision, reliability, specificity and reproducibility of the assay are established by means well known to those skilled in the art.

If the assays detect the presence of INPP5D-ATG16L1 fusion protein or mRNA, the following treatments may be administered.

The goal of inflammatory bowel disease (IBD) treatment is to reduce the inflammation that triggers symptoms. In the best cases, this may lead not only to symptom relief but also to long-term remission and reduced risks of complications. IBD treatment usually involves either drug therapy or surgery.

Doctors use one of two approaches to treatment. "Step-up" starts with milder drugs first, whereas "top-down" gives people stronger drugs earlier in the treatment process. Researchers are actively exploring new approaches to treatment for IBD, especially as new technology becomes available. Investigators suggest links between diet, the immune system and bacteria in the digestive tract (microbiome).

Anti-inflammatory drugs are often the first step in the treatment of inflammatory bowel disease. Exemplary anti-inflammatory drugs include, without limitation, aminosalicylates, corticosteroids, methotrexate, Natalizumab (Tysabri) and vedolizumab (Entyvio), and Ustekinumab (Stelara).

Aminosalicylates, such as sulfasalazine (Azulfidine), can be effective in reducing symptoms of ulcerative colitis and for some people with Crohn's disease confined to the colon, but it has a number of side effects, including digestive distress and headache. Certain 5-aminosalicylates—including mesalamine (Asacol, Lialda, Rowasa, Canasa, others), balsalazide (Colazal) and olsalazine (Dipentum)—are available in both oral and enema or suppository forms. Which form one takes depends on the area of the colon that's affected. Rarely, these medications have been associated with kidney and pancreas problems.

Corticosteroids, which include, for example, prednisone and hydrocortisone, are generally reserved for moderate to severe ulcerative colitis or Crohn's disease that doesn't respond to other treatments. They are given orally, intravenously, or by enema or suppository, depending on the part of the digestive tract affected. Corticosteroids have numerous side effects, including a puffy face, excessive facial hair, night sweats, insomnia and hyperactivity. More-serious side effects include high blood pressure, diabetes, osteoporosis, bone fractures, cataracts, glaucoma and increased chance of infection. They are not usually given long term.

Methotrexate (Rheumatrex)—which is used mainly to treat cancer, psoriasis and rheumatoid arthritis—is sometimes used for people with Crohn's disease who do not respond well to other medications. It is given by injection. Short-term side effects include nausea, fatigue and diarrhea, and rarely, it can cause potentially life-threatening pneumonia. Long-term use can lead to bone marrow suppression, scarring of the liver and sometimes cancer.

Natalizumab (Tysabri) and vedolizumab (Entyvio) work by stopping certain immune cell molecules—integrins—from binding to other cells in your intestinal lining. These drugs are approved for people with moderate to severe Crohn's disease and ulcerative colitis with evidence of inflammation who are not responding well to any other medications. Because natalizumab is associated with a rare but serious risk of progressive multifocal leukoencephalopathy—a brain infection that usually leads to death or severe disability—one must be enrolled in a special restricted distribution program to use it. Vedolizumab recently was approved for Crohn's disease. It works like natalizumab but appears not to have a risk of brain infection.

Ustekinumab (Stelara) is used to treat psoriasis. Studies have shown it is useful in treating Crohn's disease as well and may be used when other medical treatments fail.

Immune system suppressors will also reduce inflammation, but they target the immune system rather than directly treating inflammation. They suppress the immune response that releases inflammation-inducing chemicals in the intestinal lining. For some people, a combination of these drugs works better than one drug alone. Immunosuppressant drugs include, without limitation, azathioprine, mercaptopurine, cyclosporine, infliximab, adalimumab, and golimumab.

Azathioprine (Azasan, Imuran) and mercaptopurine (Purinethol, Purixan) are the most widely used immunosuppressants for treatment of inflammatory bowel disease. Taking them requires close follow-up with the doctor to have one's blood checked regularly to look for side effects, including effects on the liver and pancreas. Additional side effects include lowered resistance to infection and a rare chance of developing cancers such as lymphoma and skin cancers. A blood test to determine the ability of one's body to break down the medication should be done before starting. This will help identify the risk of suppression of the bone marrow and help with dosing.

Cyclosporine (Gengraf, Neoral, Sandimmune) is normally reserved for people who haven't responded well to other medications. Its use is generally confined to ulcerative colitis. Cyclosporine has the potential for serious side effects—such as kidney and liver damage, seizures and fatal infections—and is not for long-term use. There is also a small risk of cancer.

Infliximab (Remicade), adalimumab (Humira) and golimumab (Simponi), called tumor necrosis factor (TNF)-alpha inhibitors, or "biologics," work by neutralizing a protein produced by one's immune system. They are for people with moderate to severe Crohn's disease or ulcerative colitis who don't respond to or can't tolerate other treatments. Infliximab is given by intravenous injection and the others by subcutaneous injection. They may be combined with other immunosuppressant medications such as azathioprine or mercaptopurine.

People with ulcerative colitis who run fevers will likely be given antibiotics to help prevent or control infection. Antibiotics can reduce the amount of drainage and sometimes heal fistulas and abscesses in people with Crohn's disease. Researchers also believe antibiotics help reduce harmful intestinal bacteria and suppress the intestine's immune system. They may be used in addition to other medications or when infection is a concern—in cases of perianal Crohn's disease, for example. However, there's no strong evidence that antibiotics are effective for Crohn's disease. Frequently prescribed antibiotics include metronidazole, and ciprofloxacin.

At one time, metronidazole was the most commonly used antibiotic for Crohn's disease. It can cause serious side effects, including numbness and tingling in the hands and feet and, occasionally, muscle pain or weakness. If these effects occur, it is necessary to stop the medication and call the doctor. One should also not drink alcohol while taking this medication because of severe side effects—including nausea, vomiting and tremor—due to the interaction of the drug with alcohol.

Ciprofloxacin (Cipro), which improves symptoms in some people with Crohn's disease, is now generally preferred to metronidazole. A rare side effect is tendon rupture, which is an increased risk if one is also taking corticosteroids.

In addition to controlling inflammation, some medications may help relieve IBD signs and symptoms, but it is wise to always talk to the doctor before taking any over-the-counter medications. Depending on the severity of one's Crohn's disease, the doctor may recommend one or more of the following: anti-diarrheal medications, pain relievers, iron supplements, vitamin B-12 shots, calcium and vitamin D supplements, or nutrition.

A fiber supplement—such as *psyllium* powder (Metamucil) or methylcellulose (Citrucel)—can help relieve mild to moderate diarrhea by adding bulk to one's stool. For more severe diarrhea, loperamide (Imodium) may be effective. Anti-diarrheal medications should only be used after discussion with the doctor.

For mild pain, the doctor may recommend acetaminophen (Tylenol, others). However, ibuprofen (Advil, Motrin IB, others), naproxen sodium (Aleve, Anaprox) and diclofenac sodium (Voltaren, Solaraze) likely will make symptoms worse and can make the disease worse as well.

If one has chronic intestinal bleeding, one may develop iron deficiency anemia and need to take iron supplements.

Crohn's disease can cause vitamin B-12 deficiency. Vitamin B-12 helps prevent anemia, promotes normal growth and development, and is essential for proper nerve function.

Crohn's disease and steroids used to treat it can increase one's risk of osteoporosis, so one may need to take a calcium supplement with added vitamin D.

The doctor may recommend a special diet given via a feeding tube (enteral nutrition) or nutrients injected into a vein (parenteral nutrition) to treat the Crohn's disease. This can improve one's overall nutrition and allow the bowel to rest. Bowel rest can reduce inflammation in the short term. If there is a stenosis or stricture in the bowel, the doctor may recommend a low-residue diet. This will help to minimize the chance that undigested food will get stuck in the narrowed part of the bowel and lead to a blockage.

If diet and lifestyle changes, drug therapy, or other treatments don't relieve IBD signs and symptoms, the doctor may recommend surgery. Surgery can often eliminate ulcerative colitis, but that usually means removing the entire colon and rectum (proctocolectomy). In most cases, this involves a procedure called ileoanal anastomosis that eliminates the need to wear a bag to collect stool. The surgeon constructs a pouch from the end of the small intestine. The pouch is then attached directly to one's anus, allowing the patient to expel waste relatively normally.

In some cases, a pouch is not possible. Instead, surgeons create a permanent opening in your abdomen (ileal stoma) through which stool is passed for collection in an attached bag.

Up to one-half of people with Crohn's disease will require at least one surgery. However, surgery does not cure Crohn's disease. During surgery, the doctor removes a damaged portion of the digestive tract and then reconnects the healthy sections. Surgery may also be used to close fistulas and drain abscesses. A common procedure for Crohn's disease is strictureplasty, which widens a segment of the intestine that has become too narrow.

The benefits of surgery for Crohn's disease are usually temporary. The disease often recurs, frequently near the reconnected tissue. The best approach is to follow surgery with medication to minimize the risk of recurrence. The doctor may recommend a repeat colonoscopy in six to 12 months to look for signs of disease and help with correct treatment.

The above described assay kits would further provide instructions for use.

The Examples are provided to aid in the understanding of the invention and are not construed as a limitation thereof.

EXAMPLES

The examples below are intended to exemplify the practice of the present invention but are by no means intended to limit the scope thereof.

Materials and Methods for Examples

RT-PCR Analysis of SHIP1-ATG16L1 Fusion Transcript.

RNA was extracted from whole blood by using the RNA blood mini Kit (Qiagen) and 200 ng of RNA was reverse-transcribed with the QuantiTect Reverse Transcription Kit (Qiagen) according to manufacturer's recommendations. PCR was performed using the following forward and reverse primers (5'-CCCATATCACCCAAGAAGTT-3' (SEQ ID NO: 8) 5'-AAATACCTTATCTCGTGCCTG-3' (SEQ ID NO: 9), respectively) were evaluated by electrophoresis on agarose gel. Primers for identification of the SHIP1: ATG16L1 transcripts were designed based on the sequence found in RNA-Seq analysis.

RNA-Seq.

Whole transcriptome profiling was performed by using a stranded RNA-Sequencing (RNA-Seq) approach by the SUNY Molecular Analysis Core (SUNYMAC) at Upstate Medical University. Total RNA was purified by using a RNeasy kit (Qiagen), followed by quantification and integrity assessment using the Agilent RNA 6000 Nano kit (Agilent Technologies). Libraries were generated by using the TruSeq Stranded Total RNA Kit (Illumina). The samples were sequenced with an Illumina NextSeq 500 instrument using 1×75 bp single end reads and a High Output V2 kit (Illumina), with a targeted average depth of coverage >30 million reads per sample. After obtaining the raw sequence reads, FASTQ files were uploaded into Illumina BaseSpace for initial quality control, summarization, and alignment performed to hg19 of the human genome using the Bowtie2 algorithm within the TopHat application. The aligned .BAM file reads were downloaded into Strand NGS (2.6) for gene fusion detection. Overall, a read depth of 32.1 million reads per sample was obtained, with 92.8% mapped to transcripts using the November 2015 Ref-Seq gene annotation model. An average of 99.4% of all reads were stranded, and approximately 75% of the reads were located fully within an exon, with the remainder non-exonic or ambiguous. When summarized by gene, there were a total of 42,497 unique genes identified in the data, encompassing 147,158 different transcripts. The present report solely uses RNA-Seq expression data on the SHIP1 and ATG16L1 transcripts.

Probe-Based Assay for Detection of Fusion Transcript.

A labeled probe-based assay was also designed to detect the fusion transcript using the following primers (5'-TACCCTCAACAGCAAACC-3' (SEQ ID NO: 10) and 5'-GGGCCAACACTGAATGA-3' (SEQ ID NO: 11), respectively) at a final concentration of 900 nM and the following HEX labeled probe 5-/SHEX/CCT CCC AGG/ ZEN/ACA CAG GAG TCA AGA TA/3IABkFQ/-3 (SEQ ID NO: 12) at a final concentration of 250 nM. This could be used for several types of PCR based assays using cDNA as template prepared from the RNA extracted from biological samples.

Example 1—A Novel mRNA Transcript Links Exon 25 of SHIP1 to Exon 2 of ATG16L1 in Most SHIP1-Deficient Subjects Sequencing of total RNA transcripts from SHIP1-deficient patients revealed the presence of a novel fusion transcript linking the SHIP1 transcript to downstream ATG16L1 transcripts in all 8 SHIP1-deficient patients analyzed by RNA-Seq (FIG. 1A). This fusion transcript was identified by subsequent RT-PCR analysis in 8 of 9 SHIP1-deficient subjects analyzed, and no fusion transcript could be identified in any of the 40 SHIP1-sufficient IBD patients or in 13 healthy control subjects analyzed (FIG. 1B). Overall, the presence of this fusion transcript represents a highly significant novel association with the SHIP1-deficient phenotype, with a conservatively estimated Odds Ratio (OR) of 153.0 (95% CI: 5.562 to 4209, p<0.0001) compared to the healthy 13 controls, and an OR of 606.3 (95% CI: 22.76-16150, p<0.0001) compared to all available SHIP1-sufficient IBD and healthy control subjects (n=53). While the molecular mechanism leading to the generation of this transcript is currently under investigation, analysis of the sequence reads indicate that it would link exon 25 of INPP5D to exon 2 of ATG16L1 (FIG. 1C). Moreover, the fusion transcript omits exon 1 of ATG16L1 and shifts the downstream reading frame leading to early truncation of the ATG16L1 protein due to the introduction of a stop codon. Translation of this fusion transcript would thus result in generation of a truncated SHIP1 protein (991 amino acids) with an apparent molecular weight of 112 kDa. The predicted sequence of this 112 kDa protein includes the SHIP1 catalytic domain but omits the protein targeting and regulatory domains normally encoded by exons 26 and 27.

Figures 2A, 2B, 2C, 2D, 2E, 2F:
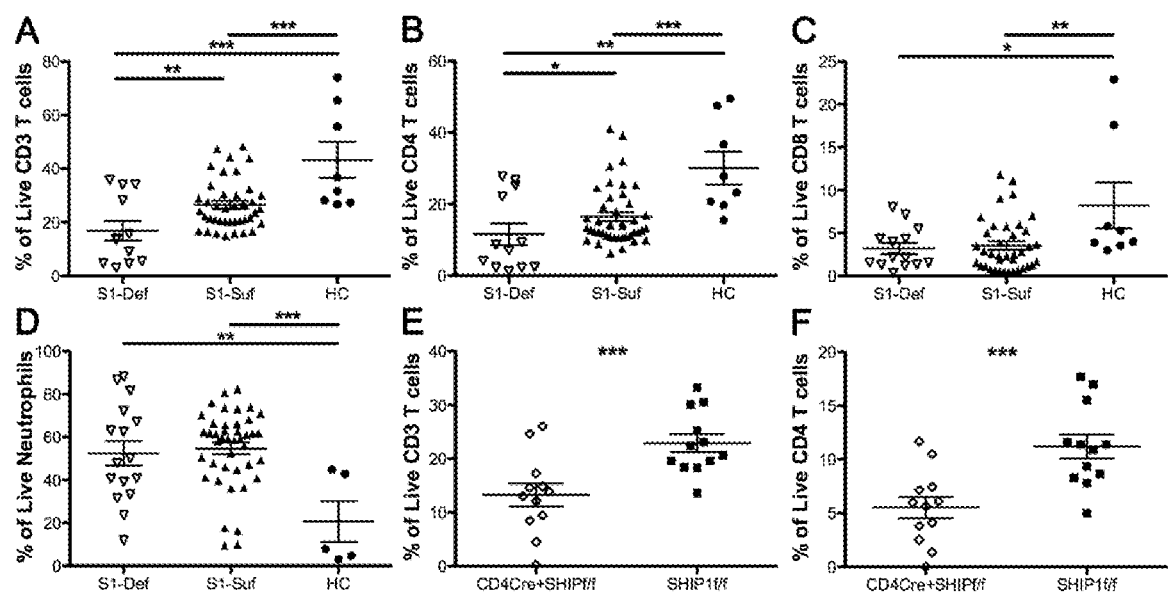
FIGS. 2A-2F show SHIP1-deficient IBD patients have significantly reduced CD4$^+$ T cell numbers relative to other IBD patients and healthy controls similar to mice with a conditional mutation of SHIP1 in T lymphocytes. Frequency of CD3$^+$ T cells (FIG. 2A), CD4$^+$ T cells (FIG. 2B), CD8$^+$ T cells (FIG. 2C), and neutrophils (FIG. 2D) were compared amongst SHIP1-deficient (S1-Def), SHIP1-sufficient (S1-Suf) and healthy control (HC) white blood cells (WBC) cultured ex vivo for 1 hour in complete media prior to icFlow staining for SHIP1. Data points were pooled from multiple independent analyses, one-tailed t-test, *p<0.05, *p<0.001, p<0.0001. Duplicate samples were analyzed for each subject. The total number of independent subjects analyzed was as follows: S1-Def=6, S1-Suf=21, HC=4.

Example 2—SHIP1-Deficient IBD Subjects and SHIP1 Conditional Mutant Mice Exhibit Profound Reductions in Circulating CD4+ T Cell Numbers The impact that SHIP1 protein loss might have on the homeostasis of circulating blood cells was next determined. A significant decrease in total $CD3^+$ T cell numbers in the blood of SHIP1-deficient was observed compared with SHIP1-sufficient IBD patients and healthy controls (FIG. 2A). This deficit was primarily due to reduced $CD4^+$ T cell numbers (FIG. 2B) although $CD8^+$ T cell frequencies were also reduced in both IBD patient subsets as compared to controls (FIG. 2C). Neutrophilia, as defined by an increased frequency of $CD15^+CD16^+$ cells, was also observed in both SHIP1-deficient and SHIP1-sufficient IBD subjects compared to healthy controls (FIG. 2D). In mice, SHIP1 deficiency in both the T cell and myeloid lineages leads to increased ileitis relative to lineage knockouts of SHIP1 in either T cells or myeloid cells alone (Maxwell et al., "SHIP-1 Deficiency in the Myeloid Compartment is Insufficient to Induce Myeloid Expansion or Chronic Inflammation," Genes Immun. 15(4):233-40 (2014), which is hereby incorporated by reference in its entirety). Mice with a T cell lineage knockout of SHIP1 also have reduced circulating $CD4^+$ T cells, demonstrating that SHIP1 is intrinsically required for the maturation or survival of circulating T cells (FIG. 2D). Since SHIP1-deficient humans also have low $CD4^+$ T cells numbers, an intrinsic role for SHIP1 in promoting normal T cell homeostasis may be conserved across species. These findings suggest that a reduction in T cell numbers combined with an increase in neutrophils might potentially contribute to increased disease severity in SHIP1-deficient subjects.

Example 3—SHIP1 Deficiency is Associated with Severe Complications of CD

Nearly 100 IBD patients were enrolled in the IBD cohort during this study and their clinical characteristics are presented in Table 1.

TABLE 1

| | Crohn's Disease | | | Ulcerative Colitis | | |
|---|---|---|---|---|---|---|
| | SHIP1-Def | SHIP1-Suf | | SHIP1-Def | SHIP1-Suf | |
| Patient number (N) | 9 | 40 | | 5 | 45 | |
| Mean Age | 56.2 | 59.6 | | 57.8 | 62.9 | |
| Mean duration of disease | 21.6 | 16.3 | | 15.8 | 22.2 | |
| Caucasian Race | 89% | 100% | | 80% | 91% | |
| Total Surgical Resections | 20 | 12 | | 0 | 10 | |
| Patients with surgery | 6 (66.7%) | 8 (20.0%) | P = 0.0106 | 0 (0.0%) | 10 (22.2%) | P = 0.5687 |
| Patients >1 surgical resection | 5 (55.6%) | 2 (5.0%) | P = 0.0027 | 0 (0.0%) | 0 (0.0%) | N/A |
| IBD related neoplasia | 2 (22.2%) | 1 (2.5%) | P = 0.0827 | 0 (0.0%) | 5 (11.1%) | P = 1.0 |
| Use of biologics | 6 (66.7%) | 17 (42.5%) | P = 0.1731 | 1 (20.0%) | 9 (13.3%) | P = 0.5457 |

The cohort was 97% male as it was recruited in a VA medical center, with an average age of 60.5. A total of 14 patients were SHIP1-deficient, including 9 with CD and 5 with UC. A history of IBD in first or second-degree relatives was significantly elicited in SHIP1-deficient 6/14 (42.9%) as compared to SHIP1-sufficient subjects 12/85 (14.1%) in the cohort (P=0.0190). A history of severe disease requiring surgical resection was more common in SHIP1-deficient CD, but not UC, subjects. There was also a non-significant trend toward increased intestinal neoplasia (dysplasia or cancer) and toward an increased use of aggressive treatments (anti-TNFα or anti-$α_4β_7$ integrin) in SHIP1-deficient CD. Together, these data suggest that SHIP1 deficiency in CD subjects, but not UC subjects is likely associated with a more aggressive disease course.

DISCUSSION

Taken together, the present findings also suggest that SHIP1 screening of both pediatric and adult IBD patients may identify those with impending severe disease that will ultimately require surgical resections. Although it did not reach statistical significance in the current cohort, more extensive analysis might also reveal an increase in IBD-associated neoplasia in SHIP1-deficient CD patients relative to other CD patients. Thus, assessments of SHIP1 expression in patients soon after diagnosis could identify CD patients who need more aggressive ("top down" rather than "step up") treatments in order to prevent future disease complications.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of detecting a fusion mRNA transcript, said method comprising:
   obtaining a biological sample from a subject;
   providing one or more reagents capable of binding a fusion mRNA transcript, wherein the fusion mRNA transcript comprises the 3' end of exon 25 of INPP5D fused to the 5' end of exon 2 of ATG16L1;
   contacting the biological sample with said reagents under conditions effective to permit binding to said fusion mRNA transcript, if present, in the biological sample; and
   detecting, based on said contacting, the fusion mRNA transcript in the sample.

2. The method according to claim 1 further comprising: identifying the subject as having IBD.

3. The method according to claim 1 further comprising: identifying the subject as having Crohn's Disease.

4. The method according to claim 1 further comprising: administering an IBD or Crohn's Disease therapeutic.

5. The method according to claim 1, wherein the biological sample is sputum, blood, a blood fraction, tissue or fine needle biopsy sample, urine, stool, peritoneal fluid, or pleural fluid.

6. The method according to claim 1, wherein said contacting is carried out using an amplification assay.

7. The method according to claim 1, wherein said contacting is carried out using a hybridization assay.

8. The method according to claim 1, wherein said contacting is carried out using an immunoassay.

9. The method according to claim 1, wherein said detecting comprises detecting the level of the fusion mRNA transcript in the sample.

10. A method of detecting a polypeptide encoded by a fusion mRNA transcript, said method comprising:
    obtaining a biological sample from a subject;
    providing one or more reagents capable of binding a polypeptide encoded by the fusion mRNA transcript, wherein the polypeptide encoded by the fusion mRNA transcript comprises the polypeptide encoded by the 3' end of exon 25 of INPP5D fused to the 5' end of exon 2 of ATG16L1;
    contacting the biological sample with said reagents under conditions effective to permit binding to said polypeptide encoded by the fusion mRNA transcript, if present, in the biological sample; and
    detecting, based on said contacting, the polypeptide encoded by the fusion mRNA transcript in the sample.

11. The method according to claim 10 further comprising: identifying the subject as having IBD.

12. The method according to claim 10 further comprising: identifying the subject as having Crohn's Disease.

13. The method according to claim 10 further comprising: administering an IBD or Crohn's Disease therapeutic.

14. The method according to claim 10, wherein the biological sample is sputum, blood, a blood fraction, tissue or fine needle biopsy sample, urine, stool, peritoneal fluid, or pleural fluid.

15. The method according to claim 10, wherein said contacting is carried out using an immunoassay.

16. The method according to claim 10, wherein said detecting comprises detecting the level of the polypeptide encoded by the fusion mRNA transcript in the sample.

17. A method of detecting a fusion mRNA transcript or polypeptide encoded by the fusion mRNA transcript, said method comprising:
    obtaining a biological sample from a subject;
    providing one or more reagents capable of binding a fusion mRNA transcript or polypeptide encoded by the fusion mRNA transcript, wherein the fusion mRNA transcript or polypeptide encoded by the fusion mRNA transcript comprises the 3' end of exon 25 of INPP5D fused to the 5' end of exon 2 of ATG16L1 or the polypeptide encoded by the 3' end of exon 25 of INPP5D fused to the 5' end of exon 2 of ATG16L1, respectively;
    contacting the biological sample with said reagents under conditions effective to permit binding to said fusion mRNA transcript or polypeptide encoded by the fusion mRNA transcript, if present, in the biological sample; and
    detecting, based on said contacting, the fusion mRNA transcript or polypeptide encoded by the fusion mRNA transcript in the sample.

* * * * *